United States

Sears et al.

4,298,594

Nov. 3, 1981

[54] XENOBIOTIC DELIVERY VEHICLES, METHOD OF FORMING THEM AND METHOD OF USING THEM

[75] Inventors: Barry Sears, Marblehead; David W. Yesair, Newbury, both of Mass.

[73] Assignee: Arthur D. Little, Inc., Cambridge, Mass.

[21] Appl. No.: 137,312

[22] Filed: Apr. 4, 1980

Related U.S. Application Data

[63] Continuation-in-part of Ser. No. 896,311, Apr. 14, 1978.

[51] Int. Cl.$^3$ .................. A61K 9/22; A61K 9/42; A61K 9/52
[52] U.S. Cl. .................................... 424/19; 424/38
[58] Field of Search .............................. 424/19, 38

[56] References Cited

PUBLICATIONS

S. K. Carter et al., International Symposium on Adriamycin, N.Y. Library of Congress No. 72-83-442 1972, Springer-Verlag.
M. Isradel, Cancer Research, 35, 1365-1368, May 1975.
A. Wade (editor) Martindale, The Extra Pharmacopoeia, 27th Ed. (1977), Pharmaceutical Press, London, pp. 1034-1035.
R. Pagano, Ann, Rev. Biophys. Bioeng. (1978) 7:435-468.
L. Krupp et al., Biochem. Biophys. Res. Comm., 72 No. 4, (1976) pp. 1251-1258.
G. Colacicco et al., Respir. Physiol., 27 (1976) pp. 169-186.
C. Kwong et al., J. Lipid Res. 12, pp. 31-35 (1971).
W. Stoffel et al., Hoppe-Seyler's Z Physiol. Chem. 3555, pp. 1367-1368 (1974).
I. Kellaway et al., Bioch. et Biophys. Acta. 144, pp. 145-148 (1967).
B. Lundberg et al., Acta Acad. Abensis, Ser. B. 34, No. 7, pp. 1-10 (1974).
M. Janiak et al., J.Mol. Biol., 86, pp. 325-329 (1974).
L. Schorr et al., Biophysics Journal, vol. 17, 81a (1977).
Krup et al. Chem. Ab. 85-189827u (1976).
Colaciccio et al., Chem. Abst. 85-155385h (1976).
Kwong et al., Chem. Abst. 74-91434m (1971).
Stoffel et al., Chem. Abst. 82-81962h (1975).
Kellaway, et al., Chem. Abst. 67-61011j (1967).
Lundberg et al., Chem. Abst. 83-54944t (1975).
Terada et al., Chem. Abst. 82-5549p (1975).
D. A. Tyrrell et al., Biochimica et Biophysica Acta, 457 (1976) 259-302.
G. Gregoriadis, New England Journal of Medicine, 295, No. 13 (1976), 704-710, 765-769.

*Primary Examiner*—Stanley J. Friedman
*Attorney, Agent, or Firm*—Richard J. Hammond

[57] ABSTRACT

A vehicle suitable for delivering a xenobiotic to a mammalian host to beneficially alter the pharmacodynamics (e.g., plasma kinetics, chemotherapeutic effectiveness, toxicity, oral absorption, tissue distribution, metabolism and the like) of the xenobiotic. The delivery vehicle is in the form of microreservoirs formed of a phospholipid constituent and a phospholipid-immiscible constituent. Xenobiotic binding agents and release agents may be added. Methods for preparing the microreservoirs containing the xenobiotic and for administering a xenobiotic to beneficially alter its pharmacodynamics are disclosed.

128 Claims, 28 Drawing Figures

○= PHOSPHATIDYL CHOLINE AND CHOLESTEROL

○= PHOSPHATIDYL CHOLINE
○~ CHOLESTEROL ESTER

○= PHOSPHATIDYL CHOLINE
○~ CHOLESTEROL ESTER

IN VITRO STABILITY OF MICRORESERVOIRS
AND PRIOR ART LIPOSOMES

IN VIVO STABILITY OF MICRORESERVOIRS

ELUTION PROFILE OF MICRORESERVOIRS-DAUNOMYCIN

PLASMA KINETICS OF MICRORESERVOIRS – DAUNOMYCIN
AND FREE DAUNOMYCIN

EFFLUX RATE OF DAUNOMYCIN FROM MICRORESERVOIRS FORMED OF PHOSPHATIDYL CHOLINE AND GLYCEROL TRIOLEATE

EFFLUX RATE OF DAUNOMYCIN FROM MICRORESERVOIRS FORMED OF PHOSPHATIDYL CHOLINE AND CHOLESTERYL OLEATE

TOXICITY OF MICRORESERVOIRS-ADRIAMYCIN AND
FREE ADRIAMYCIN

CHEMOTHERAPY OF MICRORESERVOIRS-ADRIAMYCIN AND FREE ADRIAMYCIN

ELUTION PROFILE OF MIRCORESERVOIRS-IMIDOCARB

PLASMA KINETICS OF MICRORESERVOIRS-IMIDOCARB
AND FREE IMIDOCARB - DOSE OF 5MG/KG

PLASMA KINETICS OF MICRORESERVOIRS-IMIDOCARB AND FREE IMIDOCARB-DOSE OF 4.4 MG/KG

ELUTION PROFILE OF VESICULAR AND NONVESICULAR MICRORESERVOIRS-ESTRADIOL UNDECANOATE

XENOBIOTIC DELIVERY VEHICLES, METHOD OF FORMING THEM AND METHOD OF USING THEM

This application is a continuation-in-part of Ser. No. 896,311 filed Apr. 14, 1978.

This invention relates to the delivery and release of xenobiotics within a mammalian host. More particularly, this invention relates to xenobiotic delivery vehicles in the form of circulating microreservoirs, to a method of forming the microreservoirs, and to a method of delivering xenobiotics to a mammalian host which predetermines and controls the pharmacodynamics of the xenobiotics so delivered and released.

In many different situations and under many varied circumstances it is desirable to introduce into a mammalian host pharmacologically active agents which are foreign to the host, these agents hereinafter being termed "xenobiotics." These xenobiotics include, but are not necessarily limited to, drugs, diagnostic agents, blood substitutes, endogenous biological compounds, hormones, immunological adjuvants and the like.

In the administration of any xenobiotic a certain degree of specificity must be attained, and specificity requires that the xenobiotic reach its target selectively and controllably. The absence of specificity associated with the use of many xenobiotics can thus deprive them of an appreciable part, if not essentially all, of their potential effectiveness in attaining the results desired from their use. For example, a chemotherapeutic drug which cannot be retained by blood plasma for a time sufficient for an appreciable amount of the drug to reach the target tissue or an orally administered drug which is destined for the blood stream but which cannot pass through the gastrointestinal tract lacks the degree of specificity which could make it highly effective. Thus in lacking the desired specificity, a xenobiotic may exhibit essentially none or only a limited degree of the pharmacodynamics desired to realize its full potential. Among such pharmacodynamics may be listed plasma kinetics, tissue distribution, degree of toxicity, levels of therapeutic drugs in vivo, solubility of xenobiotics normally incompatible with other pharmaceutical formulations, and metabolic activation of the xenobiotics.

In the prior art it has been recognized that it would be desirable to beneficially alter and control the specificity or pharmacodynamics of many of the xenobiotics found to have desirable properties. One prior art approach to controlling the specificity of drugs involves the use of implant devices located, normally through a surgical procedure, in or near the organ to which the drug is to be delivered. Typically, these implant devices comprise a covalent matrix material containing the drug to be delivered. These matrix materials may be water-soluble (e.g., carboxymethyl cellulose or polyvinyl alcohol), water-swellable (e.g., hydrogels or gelatin), hydrolytic polymers (e.g., polylactic acids, polyglycolic acids or poly-α-amino acids), or nonhydrolytic polymers (e.g., organopolysiloxane rubber). Generally, although these implant devices can control the rate at which the drug they contain can be delivered through diffusion or hydrolysis, they can exercise little if any alteration of the pharmacodynamics of the drug released.

One of the more recent approaches suggested for the alteration and control of the pharmacodynamics of xenobiotics is the use of a carrier capable of delivering and controllably releasing the xenobiotics at the site of action within the host to which the xenobiotics are administered. The use of liposomes has been proposed as carriers for this purpose. (See Gregoriadis, G., "The Carrier Potential of Liposomes in Biology and Medicines," *The New England Journal of Medicine*, Vol. 295, No. 13, pp 704–710 [Sept. 23, 1976] and No. 14, pp 765–769 [Sept. 30, 1976].) These prior art liposomes are composed of phospholipids, and especially of phsophatidyl choline in combination with other lipids such as cholesterol, dicetyl phosphate, stearyl amine and other phospholipids such as phosphatidyl serine with which the phosphatidyl choline is readily miscible. The liposomes are characterized by the miscibility of the carrier components, a fact which means that there can be little or no phase separation between such components. Furthermore, these carriers lack any high degree of stability, due primarily to the oxidation of the phospholipid components and/or their thermal or thermodynamic instability, especially when they are sonicated to a small size, e.g., about 250 Å. Moreover, those liposomes which carry a negative charge, due to the presence of dicetyl phosphate, phosphatidyl serine or other negatively charged components, will aggregate in the presence of divalent cations. Finally, when liposomes are injected intravenously, they are preferentially concentrated in the liver and spleen, due at least in part to their large size. Thus, although the prior art liposome carriers are compatible with a number of drugs and are biocompatible with the mammalian system, their inherent instability, tendency to aggregate materially, and relatively large size detract from their ability to serve as acceptable drug delivery systems.

Because of the ever-increasing role played by xenobiotics in the treatment of cancer, diabetes, arthritis, inherited metabolic disorders, metal-storage diseases, and the like, in the prevention of such diseases as anaplasma and of virus infections, and in the study of biological mechanisms the need for improved carriers is an ever-growing one. The desirability of having such improved delivery systems is therefore apparent.

It is therefore a primary object of this invention to provide improved xenobiotic delivery vehicles in the form of microreservoirs capable of circulating within the host system. Another object is to provide xenobiotic delivery vehicles of the character described which are compatible with a wide variety of xenobiotics including hydrophobic, hydrophilic or a combination of hydrophobic and hydrophilic compounds and which are nontoxic and biocompatible with the host system. A further object of this invention is to provide xenobiotic delivery vehicles which are stable over extended periods of storage as well as in their use within the host system and amenable to various techniques of administration including oral, intravenous, intramuscular, intraperitoneal, subcutaneous, topical and inhalation.

Another object of this invention is to provide xenobiotic delivery vehicles capable of predeterminably and beneficially altering and controlling the pharmacodynamics of the xenobiotic delivered and released within the host system. Among the pharmacodynamics thus beneficially altered and controlled are plasma kinetics, tissue distribution, toxicity, oral absorption, chemotherapeutic ability, metabolism and the like.

It is another primary object of this invention to provide a method of forming xenobiotic delivery vehicles, in the form of microreservoirs, capable of circulating within a mammalian host thereby to deliver the xenobiotic at a predetermined site by effecting a predetermined beneficial alteration in the pharmacodynamics of the xenobiotics.

Yet another primary object of this invention is to provide a method for delivering and releasing a pharmaceutically effective amount of a xenobiotic within a mammalian host in a manner to exercise some predeterminable control over the delivery site, thus enhancing the effectiveness of the xenobiotic.

Other objects of the invention will in part be obvious and will in part be apparent hereinafter.

According to one aspect of this invention there is provided a delivery vehicle incorporating a xenobiotic and being biocompatible with a mammalian host to deliver and release within the aqueous environment of the host the xenobiotic, the pharacodynamics of which are beneficially altered by reason of its delivery by and release from the vehicle, the delivery vehicle being in the form of microreservoirs comprising a phospholipid constituent and a phopholipid-immiscible lipid constituent present in an amount exceeding that which is miscible with the phospholipid constituent thereby imparting to the delivery vehicle a structure in which contact between the phospholipid-immiscible lipid constituent and the aqueous environment is minimized to impart to the delivery vehicle in vitro and in vivo stability, thereby providing for the controlled release of the xenobiotic therefrom.

According to another aspect of this invention there is provided a method of forming a delivery vehicle for delivering to and releasing within the aqueous environment of a mammalian host a xenobiotic, the pharmacodynamics of which are predeterminably altered and controlled, comprising the steps of forming microreservoirs of a composition comprising a phospholipid constituent and a phospholipid-immiscible lipid constituent present in an amount exceeding that which is miscible with the phospholipid constituent to form the microreservoirs having a structure in which contact between the phospholipid-immiscible lipid constituent and the aqueous environment is minimized to impart to the delivery vehicle in vitro and in vivo stability; and incorporating the xenobiotic to be delivered within the microreservoirs.

According to yet another aspect of this invention there is provided a method of controllably delivering to and releasing a xenobiotic within the aqueous environment of a mammalian host, comprising the step of introducing into the mammalian host a pharmaceutically effective amount of a xenobiotic contained within microreservoirs formed of a phospholipid constituent and a phospholipid-immiscible lipid constituent present in an amount exceeding that which is miscible with the phospholipid constituent thereby imparting to the delivery vehicle a structure in which contact between the phospholipid-immiscible lipid constituent and the aqueous environment is minized to impart to the microreservoirs in vitro and in vivo stability, thereby providing for the controlled release of the xenobiotic therefrom.

According to still another aspect of this invention there is provided a method of predetermining and controlling the pharmacodynamics under which a xenobiotic is delivered within the aqueous environment of a mammalian host, comprising the step of releasing the xenobiotic within the host from circulating microreservoirs formed of a phospholipid constituent and a phospholipid-immiscible lipid constituent present in an amount exceeding that which is miscible with the phospholipid constituent thereby imparting to the delivery vehicle a structure in which contact between said phospholipid-immiscible lipid constituent and the aqueous environment is minimized to impart to the microreservoirs in vitro and in vivo stability, thereby controlling the pharmacodynamics of the xenobiotic.

The invention accordingly comprises the several steps and the relation of one or more such steps with respect to each of the others, and the composition and article possessing the features, properties, and the relation of constituents, which are exemplified in the following detailed disclosure, and the scope of the invention will be indicated in the claims.

For a fuller understanding of the nature and objects of the invention, reference should be had to the following detailed description taken in connection with the accompanying drawings in which FIG. 1 is a process flow chart illustrating one method of preparing the xenobiotic delivery vehicles of this invention;

Figure 13:
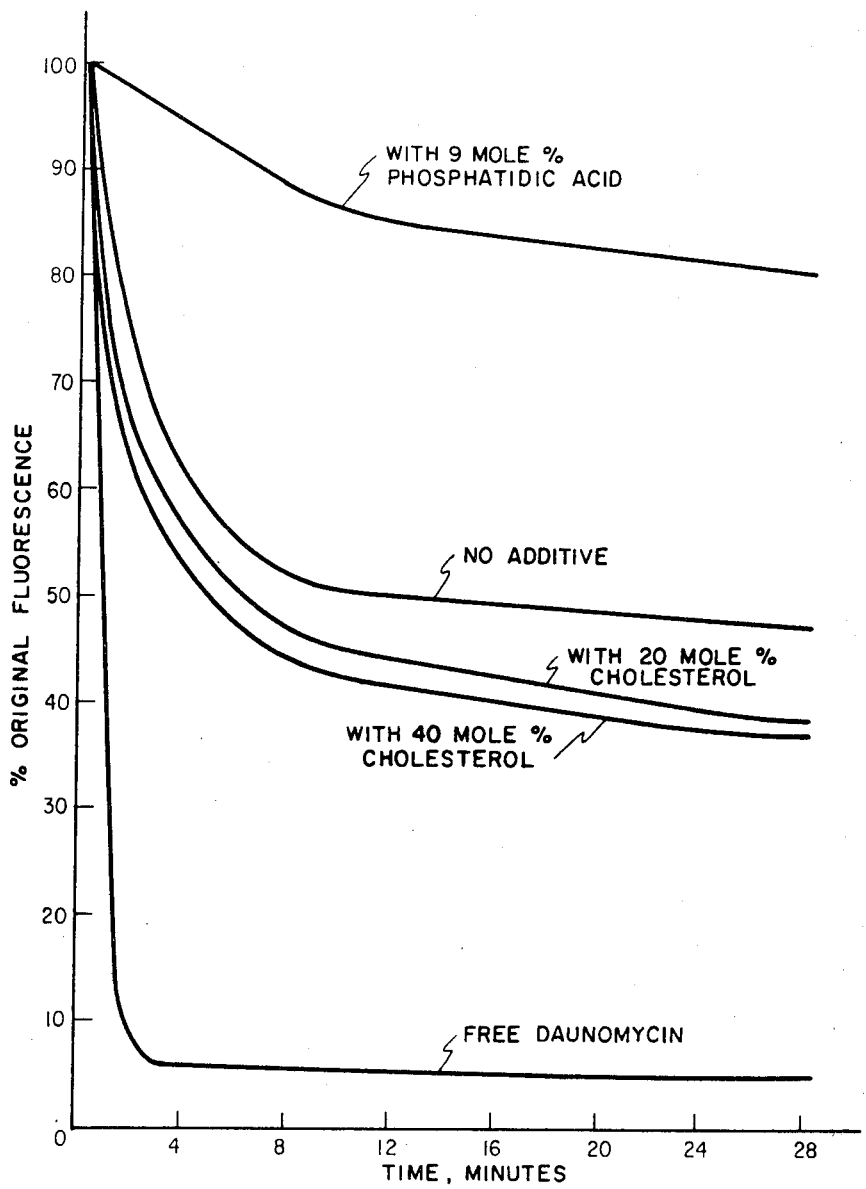
Figure 14:
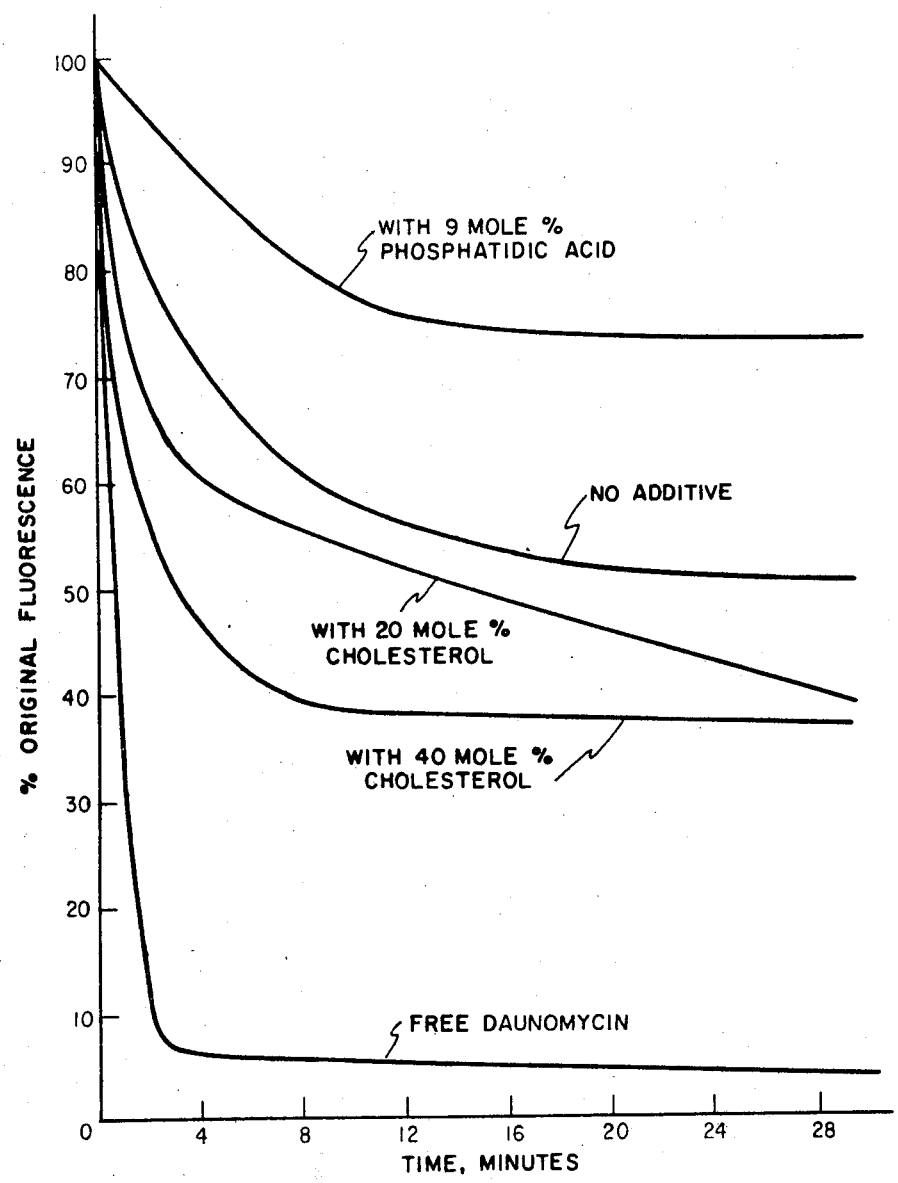
Figure 15:
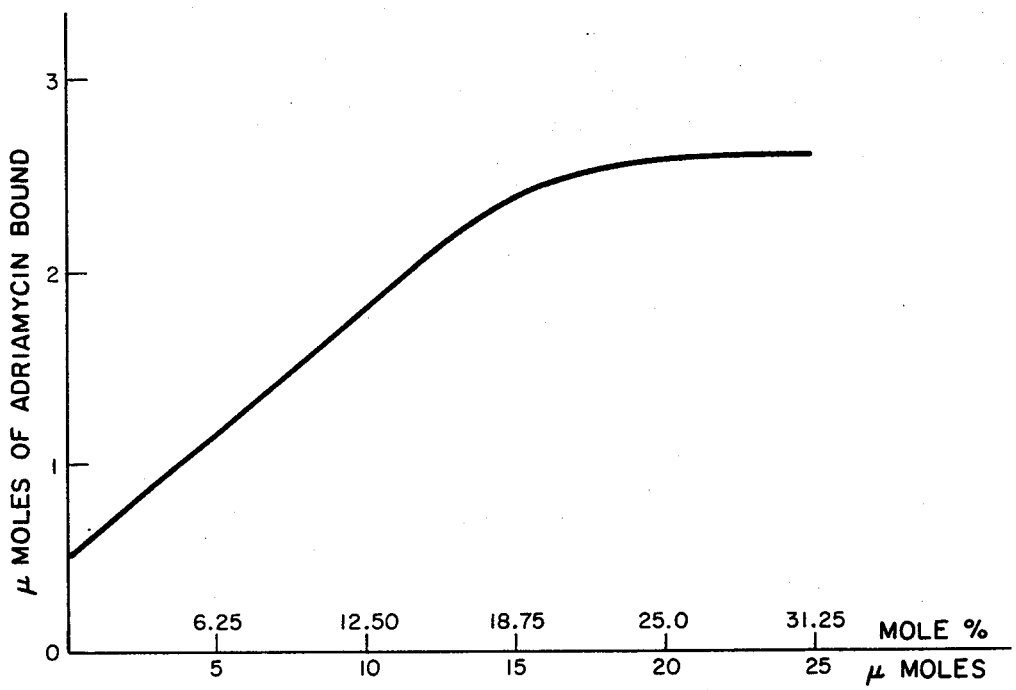
Figure 16:
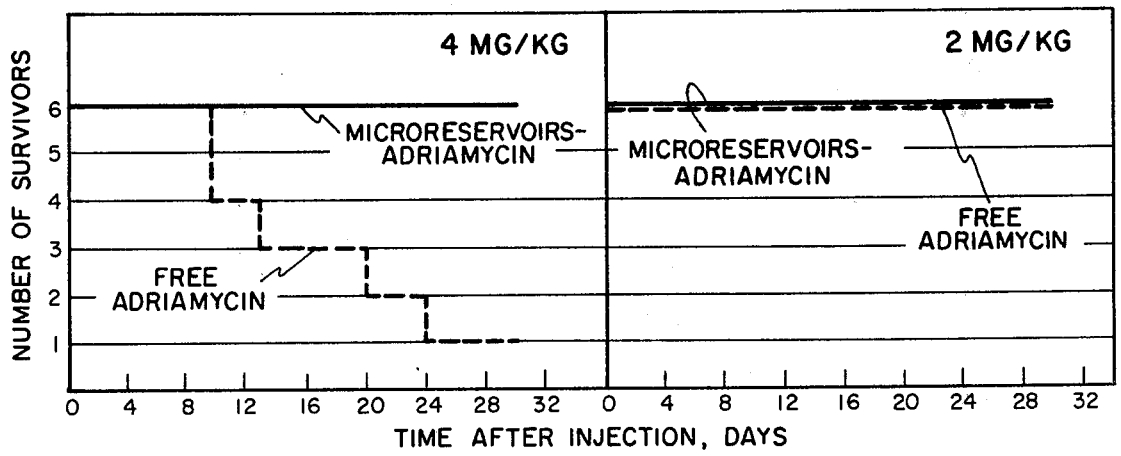
Figure 17:
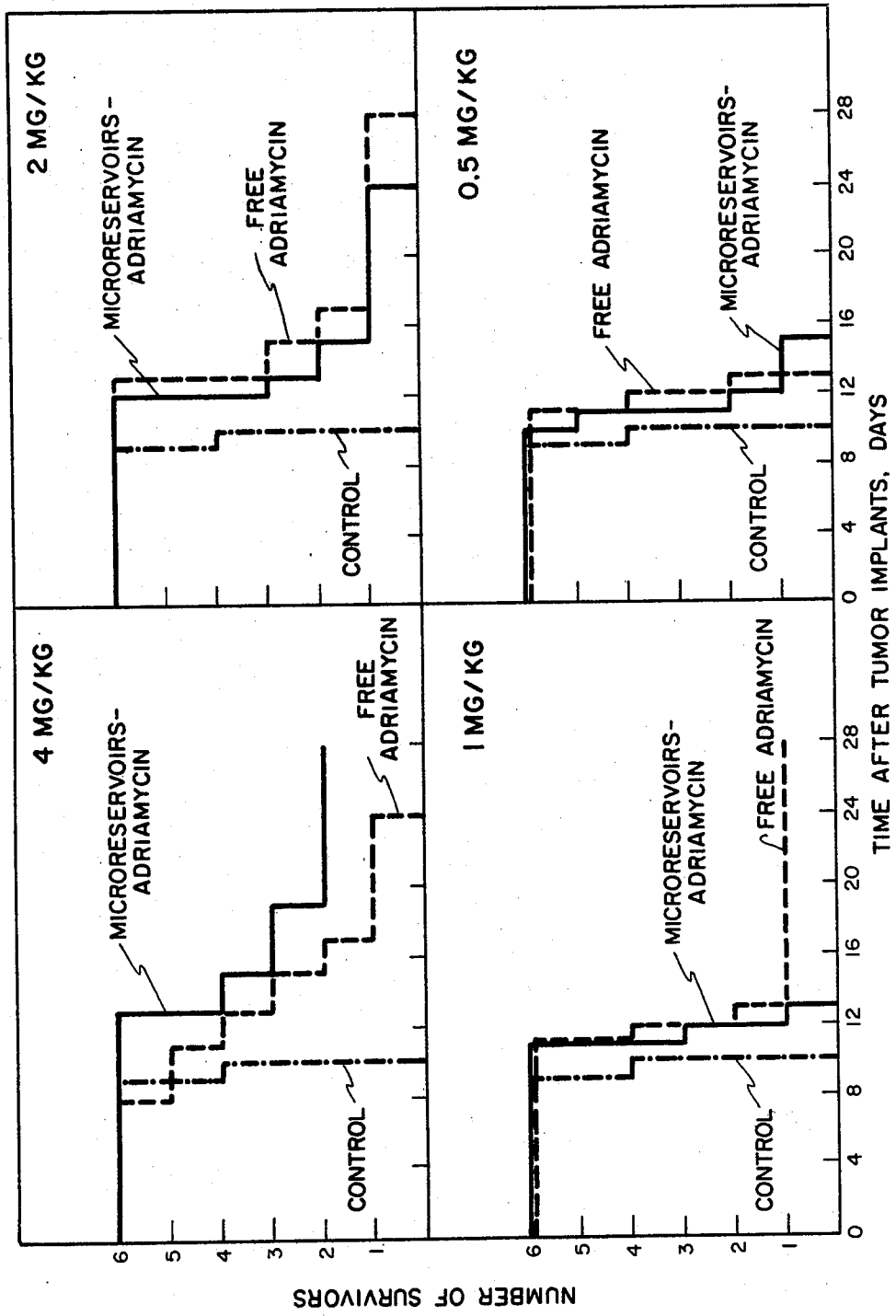
Figure 18:
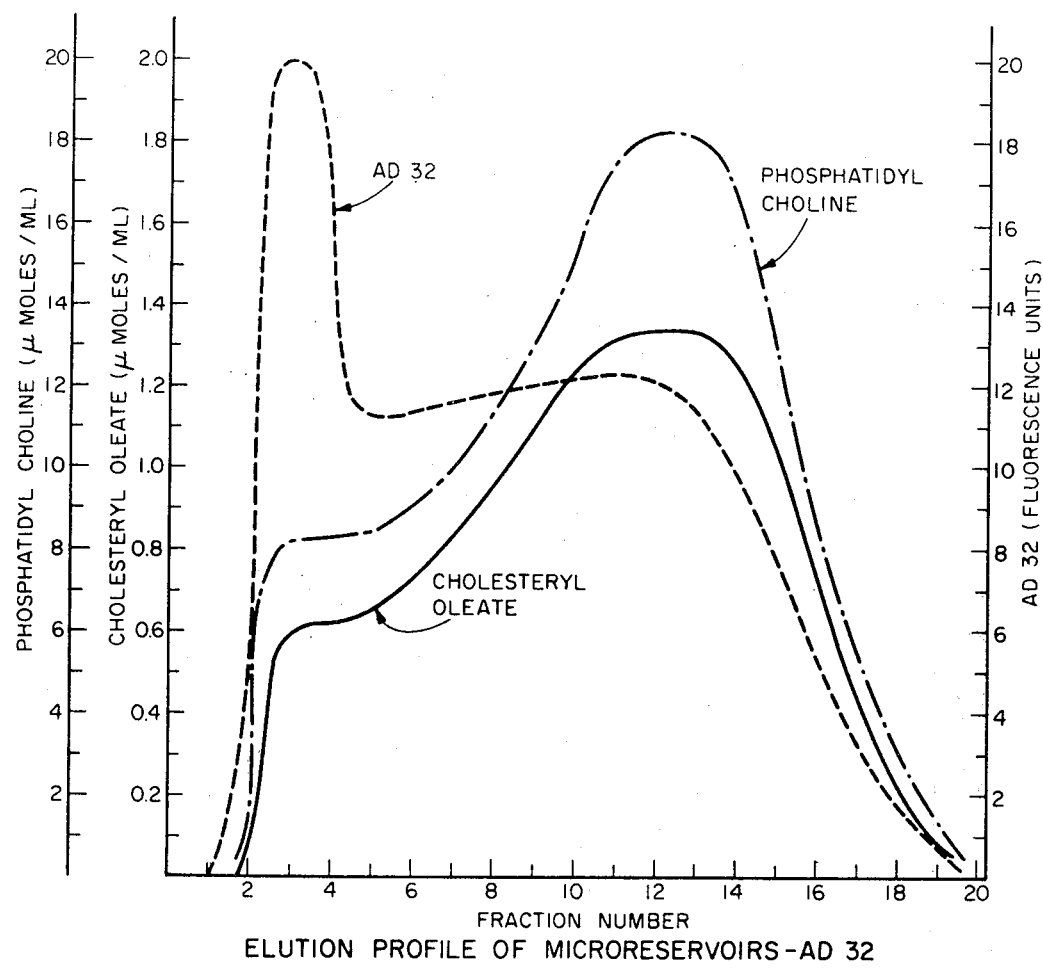
Figure 19:
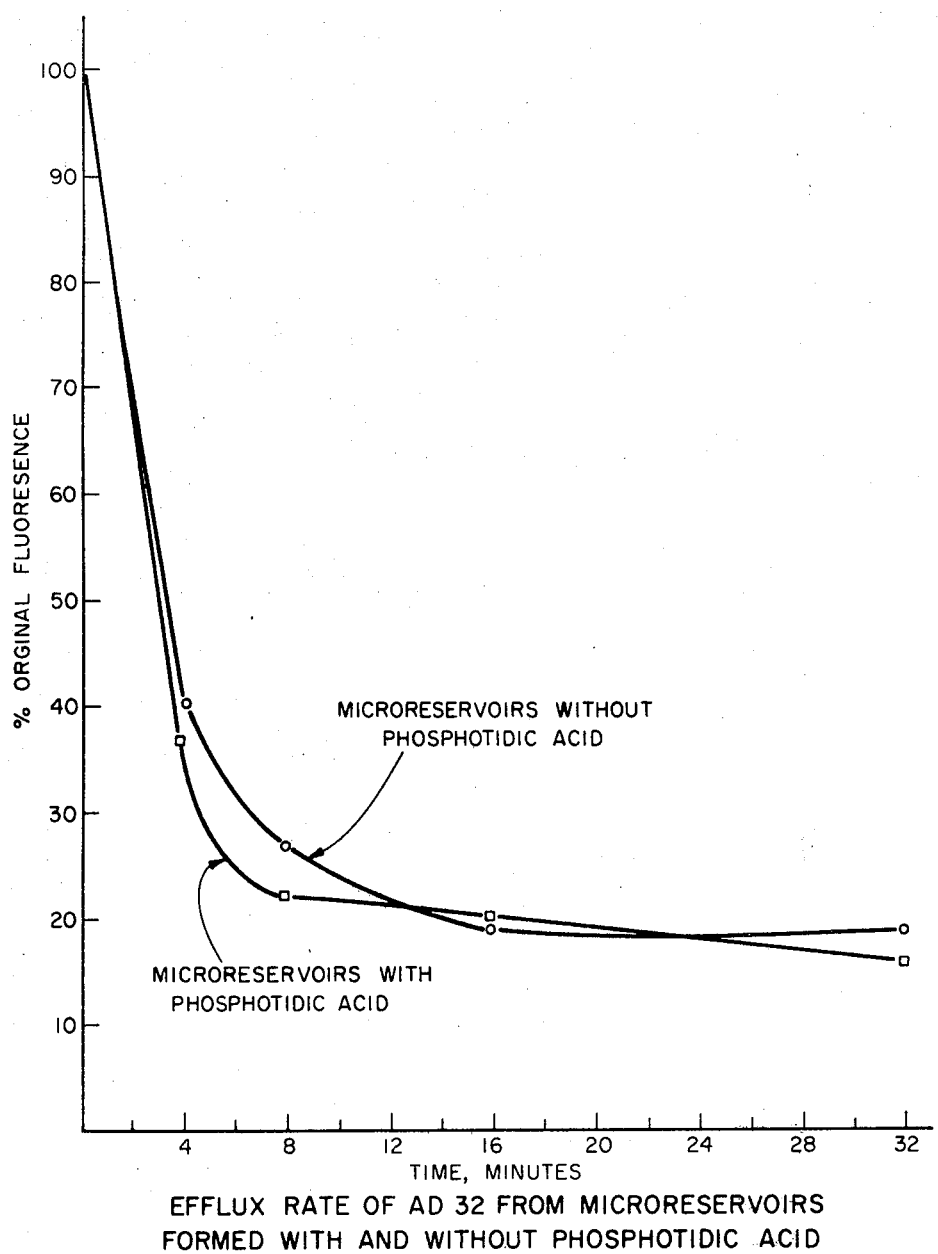
Figure 20:
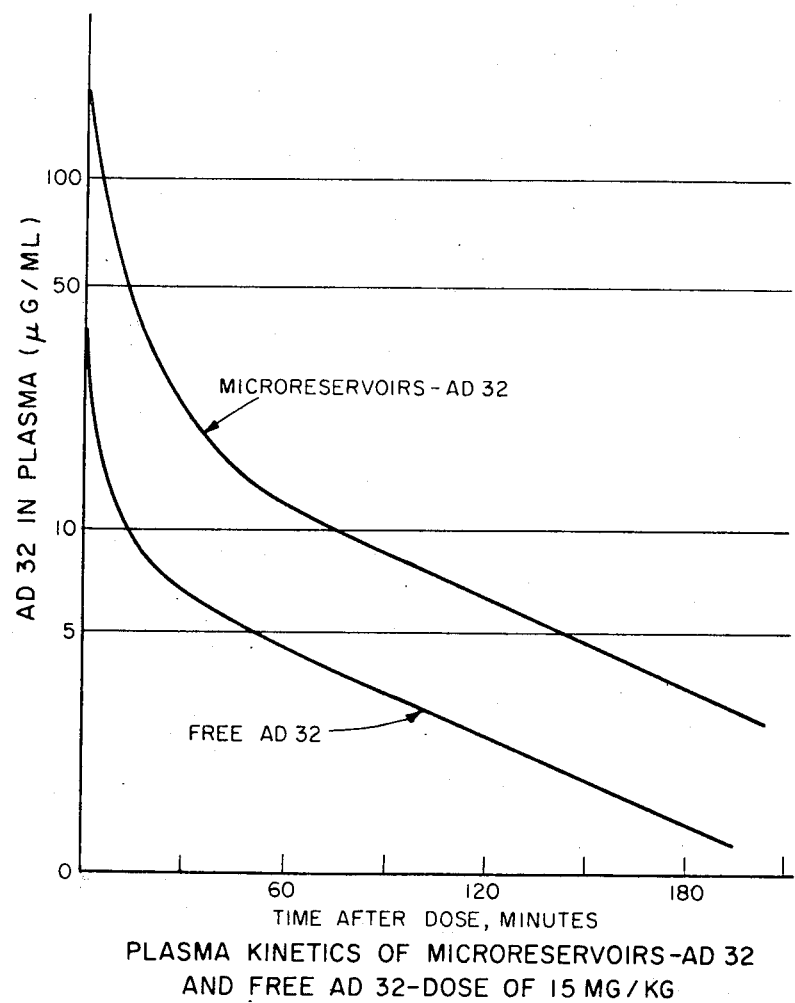
Figure 21:
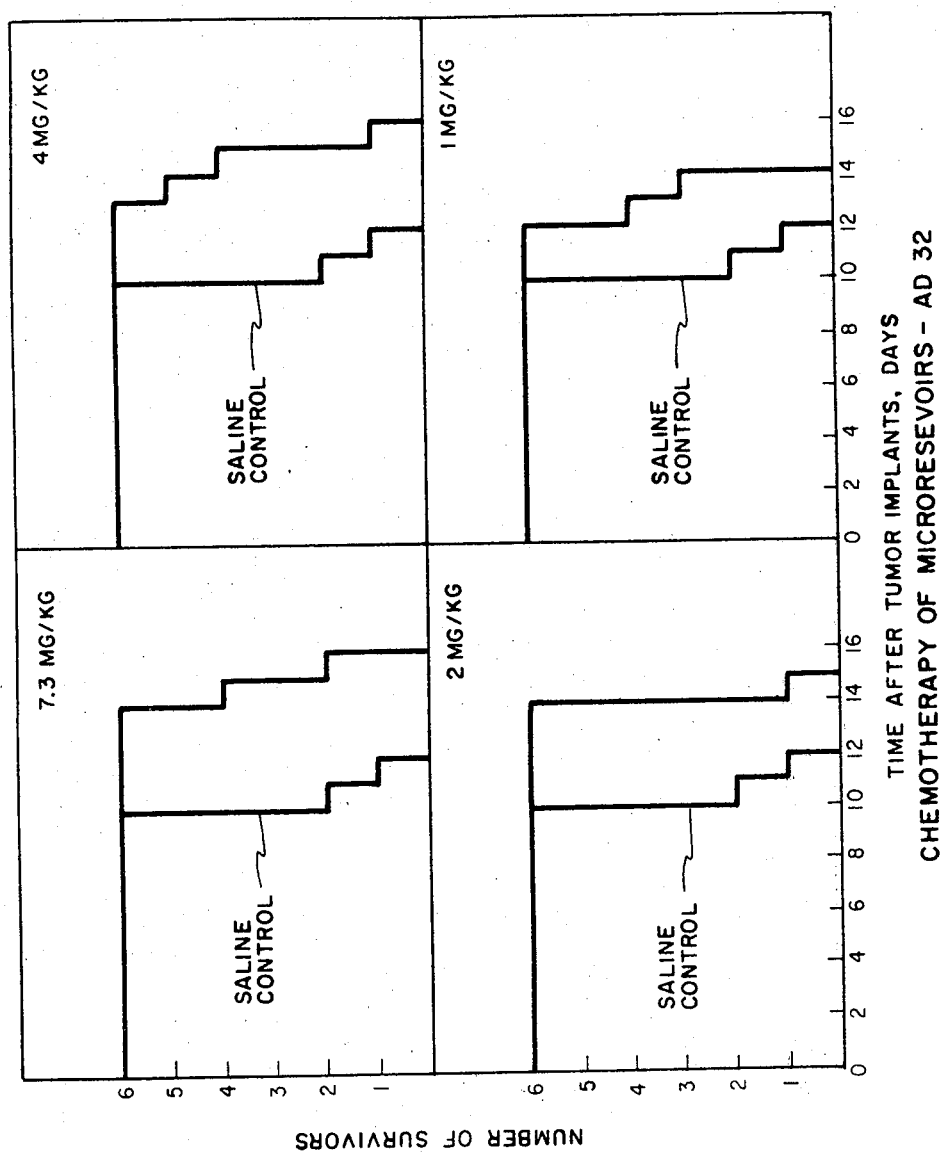
Figure 22:
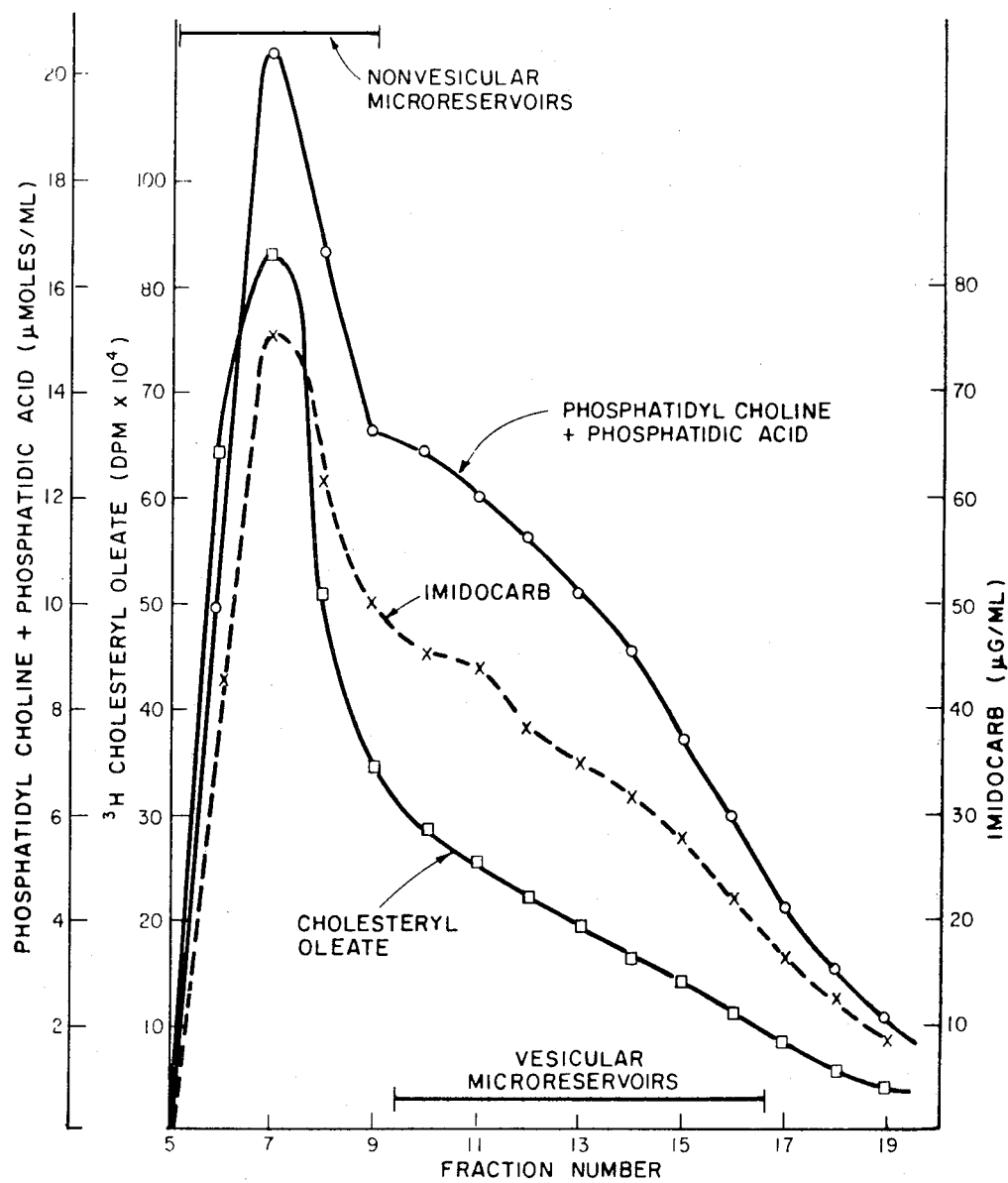
Figure 23:
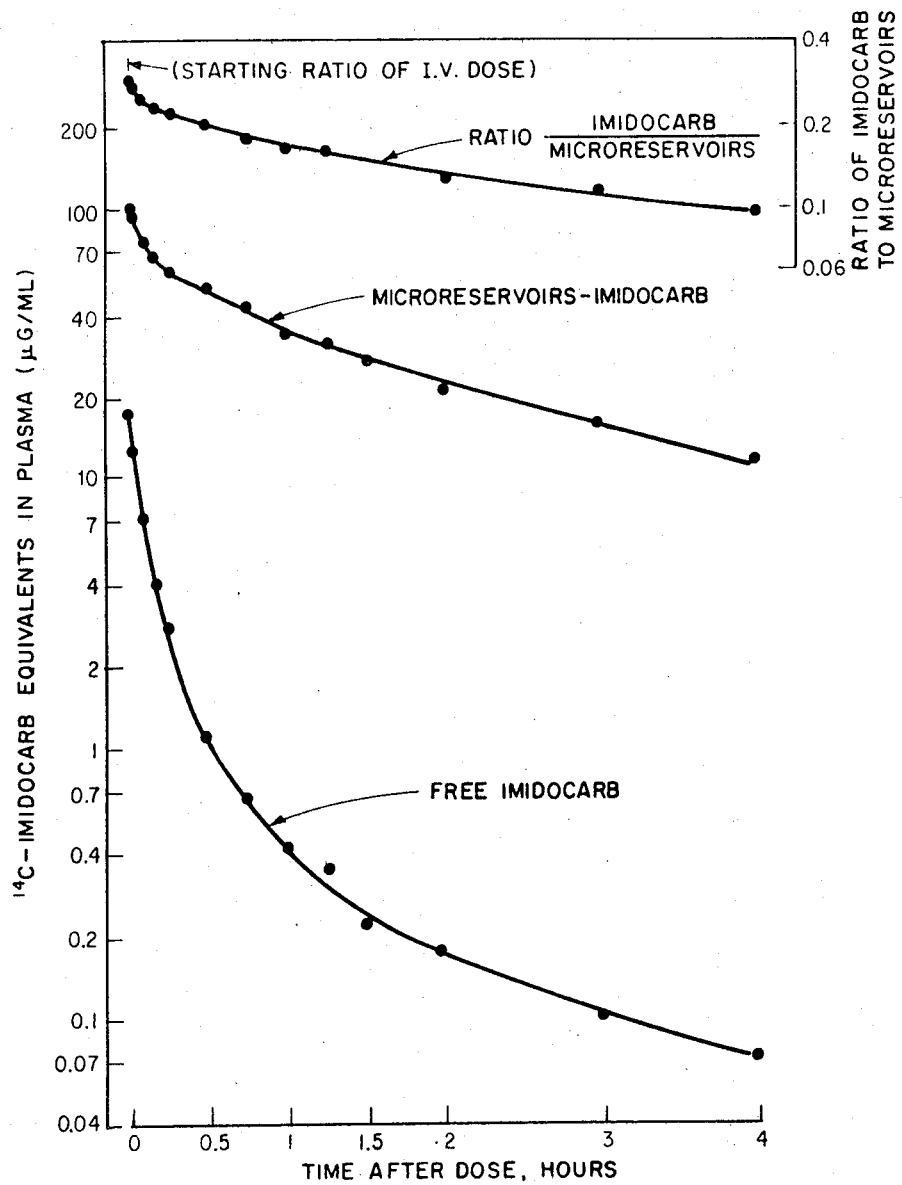
Figure 24:
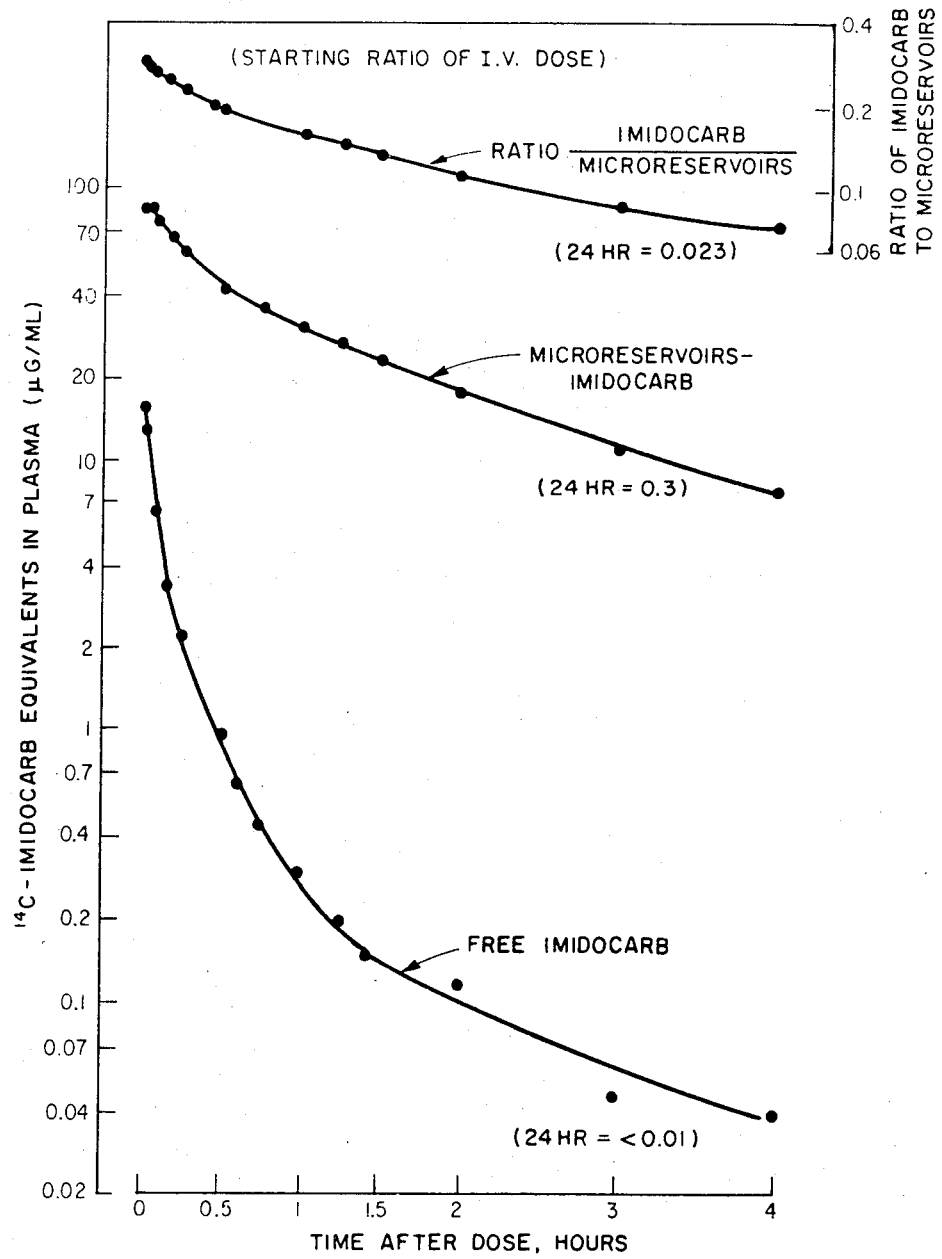
Figure 25:
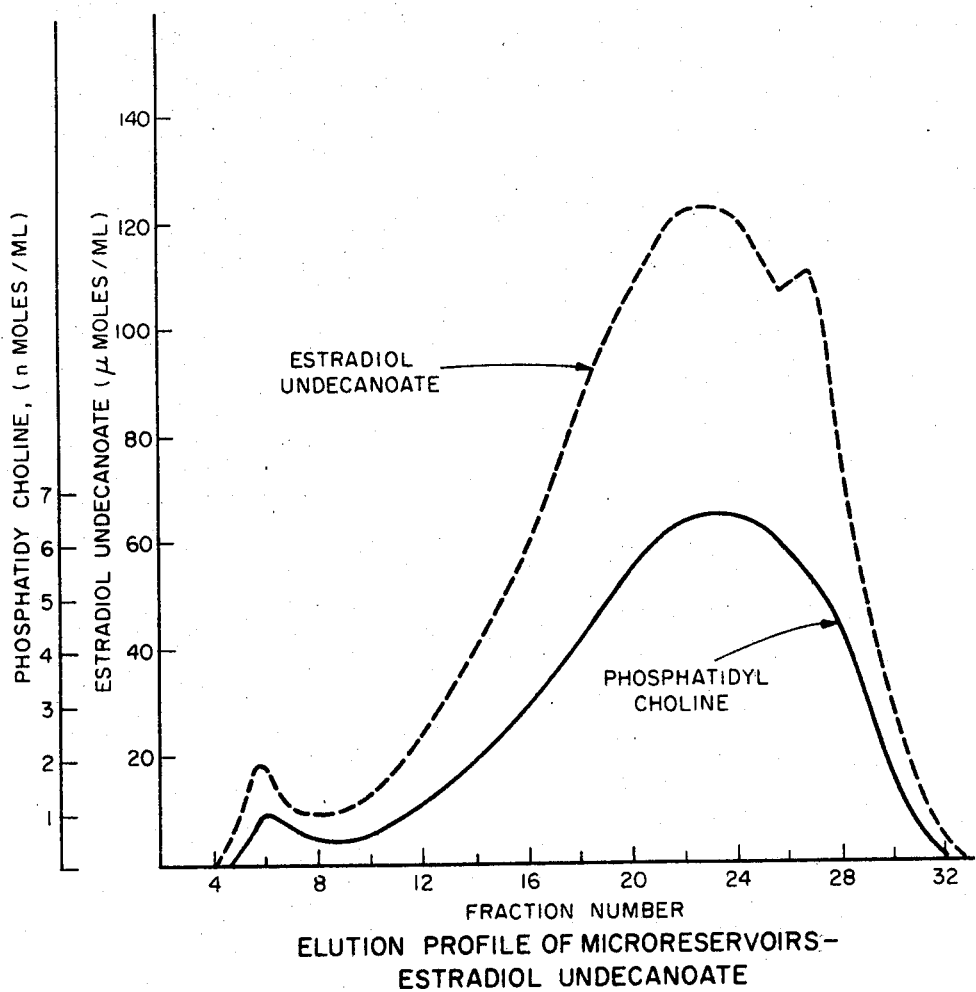
Figure 26:
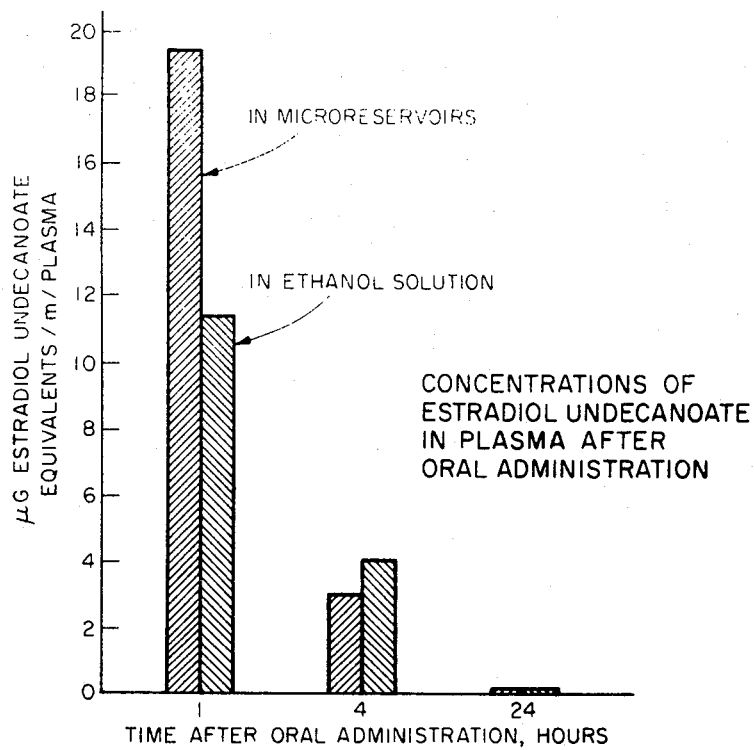
Figure 27:
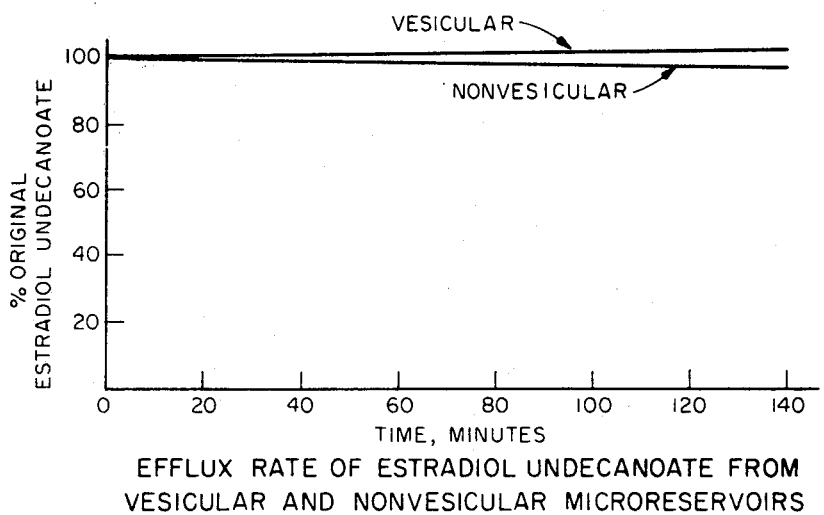
Figure 28:
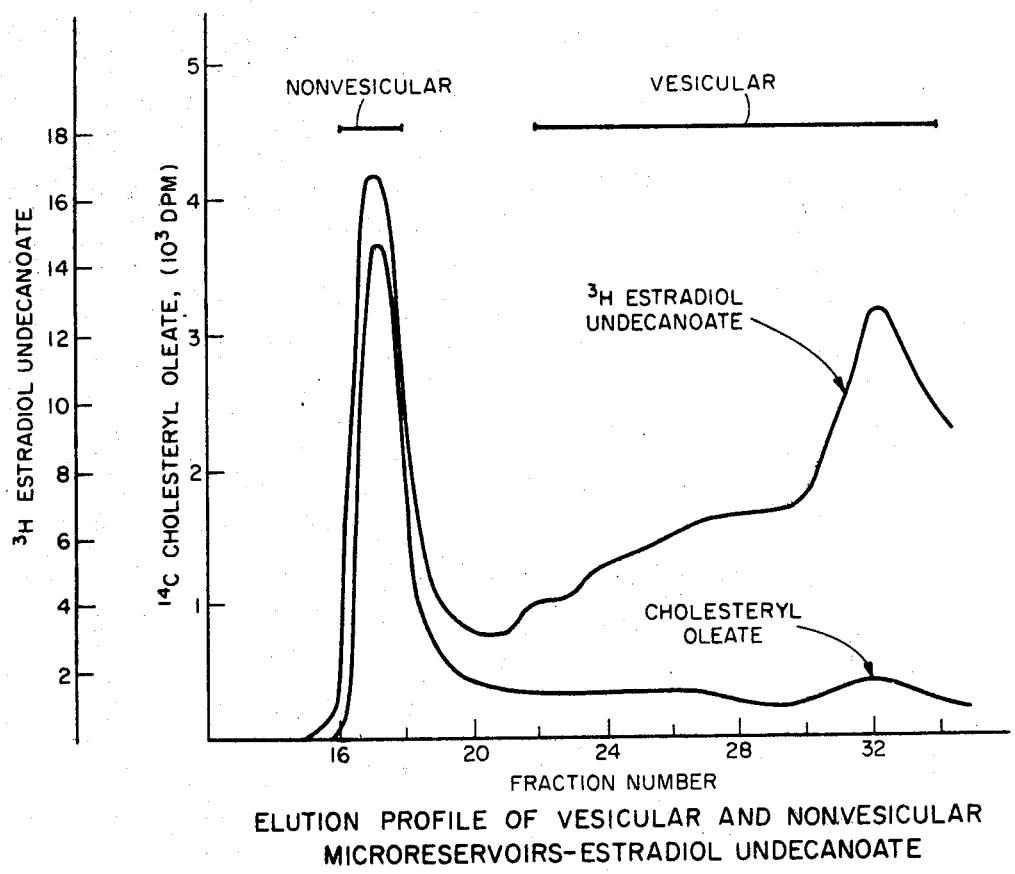

FIG. 13 comprises a series of plots of efflux rates of daunomycin as a function of time from microreservoirs of compositions containing glycerol trioleate as the phospholipid-immiscible constituent and various amounts of cholesterol as a release-rate control agent;

FIG. 14 comprises a series of plots of efflux rates of daunomycin as a function of time from microreservoirs of compositions containing cholesteryl oleate as the phospholipid-immiscible constituent and various amounts of cholesterol as a release-rate control agent;

FIG. 15 is a plot showing the effect of using a phospholipid constituent containing a phospholipid, such as phosphatidic acid, which increases the negative charge on the microreservoirs on the amount of adriamycin which can be bound into the microreservoirs;

FIG. 16 gives two plots showing the number of survivors of a group of mice as a function of time after the injection of two dose levels of adriamycin in the microreservoirs and adriamycin in free form and illustrating the ability of the microreservoirs to decrease the toxicity of the adriamycin;

FIG. 17 is a series of plots of the number of survivors of a group of mice injected with tumor cells as a function of time after the injection at four dose levels of adriamycin in the microreservoirs and in free form;

FIG. 18 is an elution profile of microreservoirs carrying AD 32 plotted as phospholipid, cholesteryl oleate and AD 32 concentrations in a series of chromatographed fractions;

FIG. 19 is a plot of the efflux rate of AD 32 from vescular microreservoirs showing the effect of using a minor amount of phosphatidic acid in the phospholipid constituent of the microreservoir composition;

FIG. 20 illustrates the extent to which the circulating microreservoirs are capable of beneficially altering the plasma kinetics of AD 32;

FIG. 21 is a series of plots of the number of survivors of a group of mice with tumor cells as a function of time after the injection at four dose levels of AD 32 in the microreservoirs, the plots illustrating the chemotherapeutic ability of AD 32 delivered by the microreservoirs;

FIG. 22 is an elution profile of microreservoirs carrying imidocarb plotted as phospholipid, cholesteryl oleate and imidocarb concentrations in a series of chromatographed fractions;

FIGS. 23 and 24 illustrate the extent to which the circulating microreservoirs are capable of beneficially altering the plasma kinetics of imidocarb at two dose levels, the illustrations being in the form of plots of the amount of imidocarb remaining in the bloodstream and the ratios of imidocarb to microreservoirs as functions of time after injection of the drug in the microreservoirs and as free imidocarb;

FIG. 25 is an elution profile of microreservoirs carrying estradiol undecanoate plotted as phosphatidyl choline and estradiol undecanoate concentrations in a series of chromatographed fractions;

FIG. 26 is a bar graph showing concentrations in blood plasma at three points in time of estradiol undecanoate given orally as an ethanol solution and in microreservoirs;

FIG. 27 is an elution profile of vesicular and nonvesicular microreservoirs carrying estradiol undecanoate; and FIG. 28 is a plot of the efflux rate of estradiol undecanoate from vesicular and nonvesicular microreservoirs.

The xenobiotic delivery vehicles of this invention are formed of a mixture of two or more lipids which are essentially immiscible. More specifically, the delivery systems are formed of compositions comprising a phospholipid constituent and a phospholipid-immiscible constituent which may be a cholesterol ester or a triglyceride or a mixture of cholesterol esters, or triglycerides or of both these constituents. The phospholipid constituent may comprise more than one phospholipid; and the microreservoir composition may also include a binding modifying and/or a release-rate controlling constituent. Exemplary of phospholipids suitable for the practice of this invention are phosphatidyl choline, phosphatidyl serine, phosphatidyl inositol, phosphatidyl ethanolamine, phosphatidic acid and sphingomyelin. Mixtures of two or more of these phospholipids may also be used. Of these, phosphatidyl choline, either alone or in admixture with other phosphalipids, is preferred.

Phosphatidyl choline is a term applied to compounds which are esters of fatty acids with glycerophosphoric acid and choline. Thus phosphatidyl choline may be represented by the following formula:

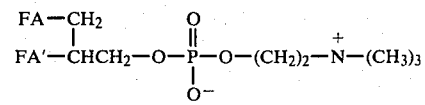

wherein FA and FA' are fatty acid residues. The fatty acids used to form these esters may be saturated or unsaturated and may contain from about 12 to 20 carbon atoms. Such fatty acids include, but are not limited to, palmitic, stearic, oleic and the like. The phosphatidyl choline used in the drug delivery vehicles of this invention may be isolated from egg yolk by the procedure described by Litman (*Biochemistry*, 12:2545[1973]) or from other natural sources such as soybeans or it may be synthesized by a suitable procedure such as that described by Robles and vander Berg (*Biochim Biophys Acta*, 187:520 [1969]).

In the following detailed description of this invention the phospholipid constituent of the delivery vehicles is illustrated, for convenience, by phosphatidyl choline, a term meant to include those esters falling within the general formula given. In some of the microreservoir formulations, minor amounts of phosphatidic acid are incorporated in the phospholipid constituents to improve the binding of the xenobiotic to the microreservoirs. It is also to be understood that other phospholipids, including those named, which meet the chemical and physical properties stated below may be used in place of the phosphatidyl choline.

The cholesterol ester or triglyceride constituent used as a component of the delivery vehicle must be essentially immiscible with the phospholipid constituent as well as essentially insoluble in an aqueous environment as represented by a physiologically-compatible liquid such as a physiologically-balanced salt solution containing NaCl or KCl. The cholesterol ester or triglyceride constituent must also be apolar or nonpolar to the degree that it will not form a monolayer and it must be present in a concentration such that it is essentially immiscible in the phospholipid bilayer.

Cholesterol, $C_{27}H_{45}OH$, is a monounsaturated, secondary alcohol which readily forms esters with both saturated and unsaturated fatty acids such as oleic, stearic, plamitic and the like. In general, fatty acids having from 10 to 18 carbon atoms are preferred. Suitable procedures for forming these cholesterol esters include the condensation of a fatty acid chloride with cholesterol or the isolation from natural sources.

In choosing the fatty acid to form the cholesterol ester, it is preferable that it is one with a minor degree of unsaturation (e.g., no greater than about two double bonds per fatty acid). In general, the esters formed of fatty acids with higher degrees of saturation form xenobiotic delivery complexes of greater stability than those formed of highly unsaturated fatty acids.

The triglycerides suitable for the practice of this invention are fatty acid esters of glycerol having the general formula

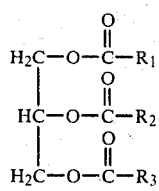

wherein $R_1$, $R_2$ and $R_3$ of the fatty acids forming the esters may have from 10 to 18 carbon atoms. Exemplary of such fatty acids are palmitic, stearic, myristic, oleic and linoleic. These triglycerides are conveniently prepared by the condensation of the fatty acid chloride with glycerol. They may also be isolated from natural sources.

In the following general description it will be assumed, for convenience, that a cholesterol ester is used. It is, of course, to be understood that a triglyceride, a mixture of cholesterol esters, a mixture of triglycerides or a mixture of one or more cholesterol esters with one or more triglycerides may also be used in forming the micro reservoir delivery vehicles. Examples are presented in which either a cholesterol ester or a triglyceride is used as the phospholipid-immiscible constituent.

The xenobiotic delivery vehicles of this invention are in the form of what are hereinafter termed "microreservoirs." These microreservoirs may assume one of two forms, namely a vesicular form which has a small walled cavity containing the medium used in making the microreservoirs, or a nonvesicular form which has the cholesterol ester and/or triglyceride contained within the phospholipid monolayer. As will be described below, the ratio of phosphatidyl choline to cholesterol ester determines which of these forms predominates in any synthetic procedure. The choice between these forms is principally dependent upon the nature of the xenobiotic to be delivered and released, the pharmacodynamics of the xenobiotic desired and the method of administration.

Figure 1:
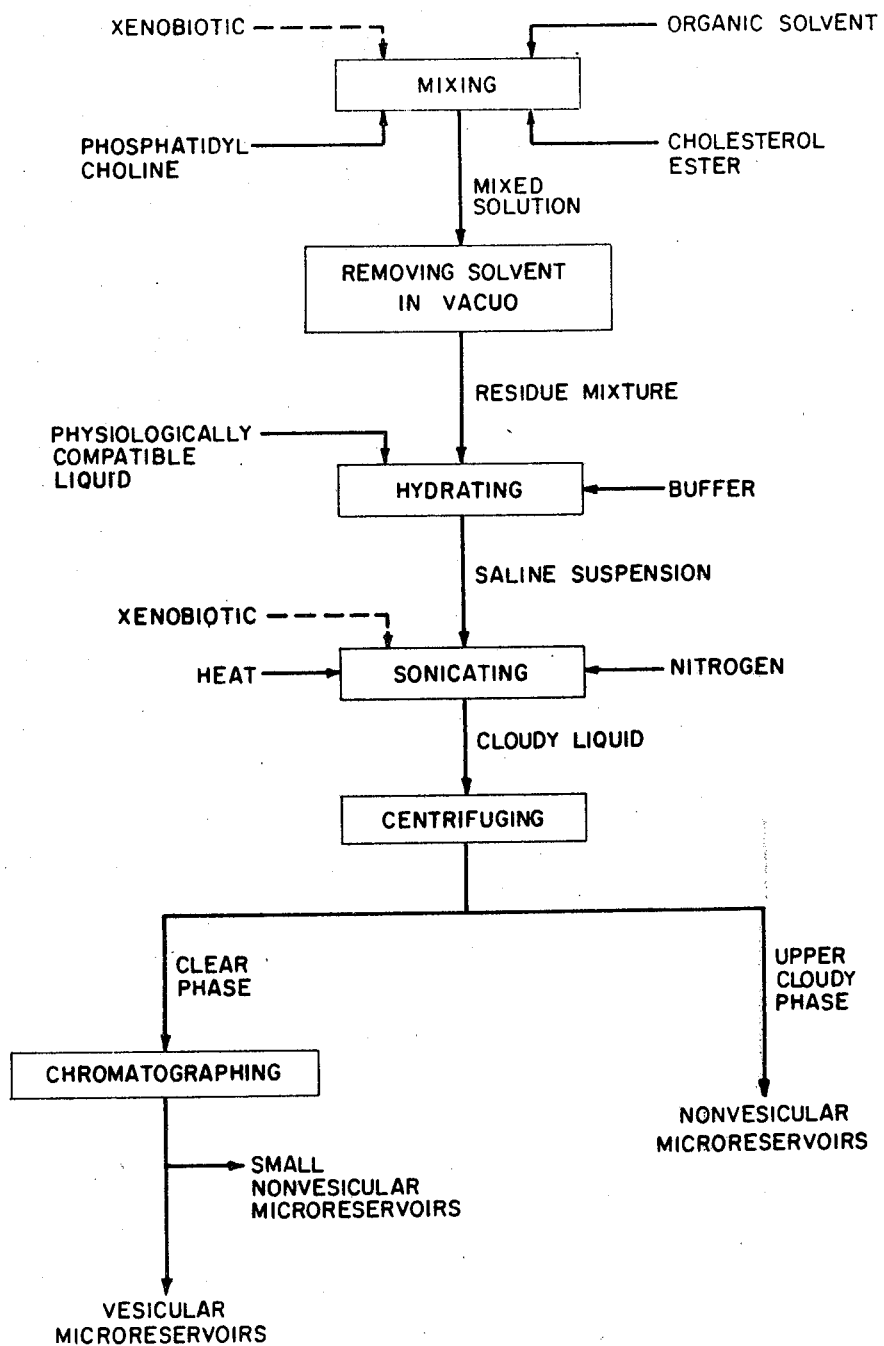
Figure 2:
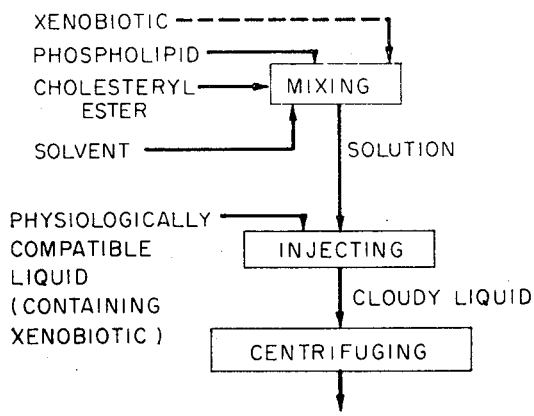
FIG. 2 is a partial process flow chart illustrating a modification of the method of FIG. 1.

Two different synthesis routes for forming the microreservoirs, along with the incorporation of the xenobiotic therein, are illustrated diagrammatically in FIGS. 1 and 2, the route shown in FIG. 1 using sonication to form the microreservoirs representing a preferred process. In this process the phosphatidyl choline and cholesterol ester are mixed in an inert organic liquid which is a solvent for both of these constituents, e.g., chloroform; and, if desired, the xenobiotic is added to this solution as indicated by a dotted line in FIG. 1. The solvent is then removed by evaporation in vacuo, leaving a dry residue mixture which is then hydrated by the addition of a physiologically-compatible liquid, as exemplified by an aqueous solution of NaCl or KCl of suitable concentration and a buffer. If the xenobiotic is not added into the initial mixture, it is added into the resulting liquid suspension prior to the formation of the microreservoirs.

In forming the liquid suspension it is preferred to use amounts of the residue mixture equivalent to between about one and about five percent by weight of the physiologically-compatible liquid. Although the amount of xenobiotic added to the phospholipid/cholesterol ester (or triglyceride) composition may vary, it is preferable to incorporate up to about two percent by residue weight of the xenobiotic in the microreservoirs.

As illustrated in FIG. 1, the microreservoirs are then formed by sonicating the saline solution under a nonoxidizing, e.g., nitrogen atmosphere. It has been found that more complete formation of the microreservoirs occurs when the sonicating is carried out at a temperature equivalent to or slightly above the melting point of the cholesterol ester or triglyceride serving as the phospholipid-immiscible constituent. The sonication is carried out at a suitable power level and for a time to produce the desired microreservoir size. For example, a power input of 120 watts for 20 minutes has been found satisfactory. As an alternative to the sonicating of the saline suspension it may be forced through a small orfice to form the microreservoirs.

As will be seen from FIG. 2, an alternative route to the formation of the microreservoirs in an aqueous medium, e.g., saline solution, lies in the formation of a solution of the phospholipid, cholesterol ester and xenobiotic using a water-miscible organic solvent and the subsequent introduction of this solution into an aqueous physiological saline solution. Alternatively, the xenobiotic may be added to the saline solution prior to the injecting step. Exemplary of this procedure is the injection of an ethanol solution of the lipid mixture into a stirred aqueous solution; or the slow injection of an ether solution of the lipid mixture into an aqueous compartment.

The cloudy liquid resulting from the formation of the microreservoirs in the aqueous suspending medium is then centrifuged to produce a clear phase and an upper cloudy phase, the latter containing larger nonvesicular microreservoirs, e.g., from about 300 Å to about 1000 Å in diameter. The clear phase is chromatographed to produce a fraction of small (e.g., about 250 Å in diameter) nonvesicular microreservoirs and vesicular microreservoirs having diameters of about 190 Å to about 300 Å.

The distribution of the microreservoirs between the vesicular and nonvesicular forms is determined by the mole ratio of phospholipid to phospholipid-immiscible constituent. Using phosphatidyl choline and cholesteryl oleate as illustrative of a microreservoir composition, it may be shown that the use of between about 67 and 97 mole % of phosphatidyl choline yields predominantly vesicular microreservoirs; while the use of more than about 50 mole % of cholesterol ester yields predominantly nonvesicular microreservoirs.

Figure 5:
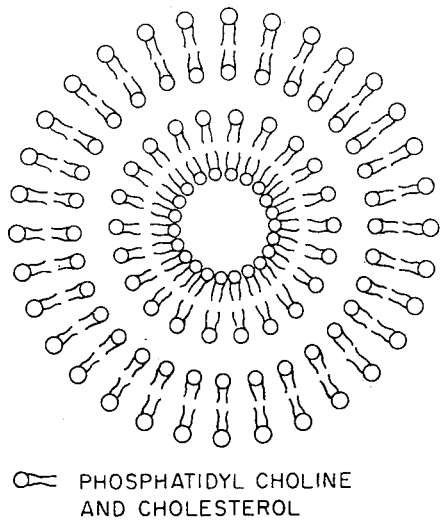
FIG. 5 is a much-enlarged diagrammatic representation of a drug delivery vehicle of the type disclosed in the prior art.

The microreservoirs of this invention have unique structural properties due to the use of a mixture of the phospholipid constituent and a lipid constituent (cholesterol ester, triglyceride or mixtures thereof) which is essentially immiscible with the phospholipid. This structure, in its vesicular and nonvesicular forms, is shown diagrammatically in FIGS. 3 and 4. The insolubility of both the phospholipids (represented by phosphatidyl choline in FIGS. 3 and 4) and the immiscible lipid constituent (represented by a cholesterol ester) gives rise to an organized microreservoir structure in which contact between the phospholipid immiscible lipid constituent and the aqueous environment is avoided or reduced to a minimum. This organization in turn imparts much greater stability to the microreservoirs than that attained by a vehicle formed in accordance with the prior art teaching of Gregoriadis previously cited. This may be shown by a comparison of FIG. 3 and 4 on one hand and FIG. 5 on the other, FIG. 5 representing diagrammatically the structure of the drug delivery system of Gregoriadis. It will be seen from FIG. 5 that when miscible lipids are used to form the liposome the result is a lamellar structure giving rise to an unstable organization due apparently to the oxidation of the phospholipids which destabilizes the lamellar organization; or to crystallization of the phospholipids if the temperature decreases below their transition temperature; or to the thermodynamic instability of small sonicated phospholipid vesicles.

Although the use of liposomes as drug delivery systems has been studied extensively, they have not been found to be effective in this role because of their in vivo instability, and their tendency to agglomerate and to concentrate in certain organs, e.g., the liver. (See for example Gregoriadis, G., "The Carrier Potential of Liposomes in Biology and Medicines" *The New England Journal of Medicine*, 295: 704–710 and 765–769 (1976); Tyrell, D. A., Heath, T. D., Colley, C. M., and Ryman, B. E., "New Aspects of Liposomes" *Biochim. Biophy. Acta*, 457: 259–302 (1976); and Pagano, R. E. and Weinstein, J. N., "Interactions of Liposomes With Mammalian Cells" in "Annual Review of Biology and Biophysics," Annual Reviews Inc., Palo Alto, Calif. (1978) pp 435–468).

The use of liposomes as drug carriers imposes on them the requirement for an aqueous space to facilitate the trapping of the drug. Unilamellar liposome vesicles (about 250 Å) suffer from not only a very low amount of aqueous space but also from thermodynamic instability. Although the multilamellar liposomes (10,000 to 50,000 Å) have a greater initial drug-trapping efficiency, they lack in vivo stability due to their structure and they are removed from circulation at very rapid rates. (Stamp, D. and Juliano, R. L., *Biochem Biophys Res. Comm.*, 63, 651 (1975).) Finally, a recent approach to the use of liposomes as drug carries has been to form large unilamellar vesicles about 2000 Å in size. (See Papahadjopoulos, D., Vail, W. J., Jacobson, K. and Poste, G., *Biochim. Biophy. Acta*, 394, 483 (1975).) However, all of these efforts put forth to form liposomes capable of carrying and controlling releasing a drug have so far been unsuccessful.

A number of publications have described the sonication of phospholipids and cholesterol esters to understand the lipid organization of lypoproteins. (See, for example, Hinz, R. and Scaner, A., *Biochim. Biophys. Acta.*, 207, 304 (1970); Scaner, A., Crump, E., Thoth, J., Kogee, S., Stiller, E. and Albers, L., *Biochemistry* 9, 1327 (1970); Scaner, A. M. and Tardieu, A., *Biochim. Biophy. Acta*, 231, (1971); Stoffel, W., Tunggol, B. D., Zuenberg, O., Schrieber, E. and Binczeh, E., Hoppe Seyler's *Z. Physiol. Chem*, 355, 1367 (1974) and Shorr, Lucy, Shipley, G. G., Small, D. M., and Sears, *Biophysical Journal*, 17: 81a (1977)).

Figure 3:
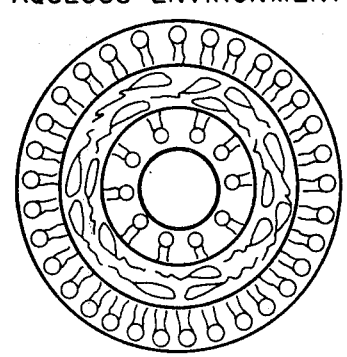
FIG. 3 is a much-enlarged diagrammatic representation of a microreservoir of this invention in vesicular form.

In the work of Shorr et al the liposomes were used as the membrane models and so called "microemulsions" served as the serum lipoproteins models, both being used to study the role of cholesterol esters in atherosclerosis. The so-called "microemulsions" were made by sonicating cholesteryl oleate and phosphatidyl choline in mole ratios of 0.5 and 1.2 (33.3 and 54.5 mole % cholesteryl oleate, respectively); and were described by Shorr et al as "consisting of a CO [cholesteryl oleate] core surrounded by a PC [phosphatidyl choline] monolayer." It is now known, however, that these so-called "microemulsions" of Shorr et al. actually comprise a core made up of a phospholipid-immiscible lipid layer, a phospholipid layer and an aqueous core as shown in FIG. 3 and can be accurately termed "vesicular microreservoirs." The larger microreservoirs ranging in size between about 300 and 1000 Å, i.e., the nonvesicular microreservoirs shown in FIG. 4, comprise a phospholipid-immiscible lipid core and a phospholipid outer layer—the structure incorrectly attributed by Shorr et al to their "microemulsions" ranging in size between about 190 and 300 Å. Shorr et al identified no utility for their incorrectly defined "microemulsions" other than that of serving as serum lipoprotein models.

Figure 4:
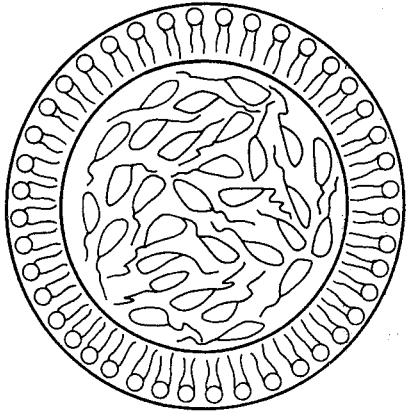
FIG. 4 is a much-enlarged diagrammatic representation of a microreservoir of this invention in nonvesicular form.

The stable structure of the microreservoirs of this invention, shown in FIGS. 3 and 4, may be attributed, at least in part, to a thermodynamic driving force which prevents the cholesterol ester or triglyceride from being exposed to the aqueous environment. As a result, the structural integrity of the microreservoirs of this invention is greatly enhanced. This, in turn, means that the potential for the microreservoirs to control and alter the pharmacodynamics of the xenobiotics incorporated in them is likewise enhanced when compared with other delivery systems. Moreover, the apolarity of the microreservoirs, which is a result of the use of cholesterol esters or triglycerides in place of cholesterol and the like, essentially prevents aggregation of the microreservoirs. This is, of course, highly desirable since such aggregation would otherwise release the cholesterol esters or triglycerides into an aqueous environment with a resulting large decrease in the free energy of the system. Thus, the individual microreservoirs, which are similar in many respects to the naturally occurring circulating serum lipoproteins, are particularly well adapted to circulate in the blood plasma of the mammalian host into which they are introduced and to remain in the plasma for maximum effectiveness.

Figure 6:
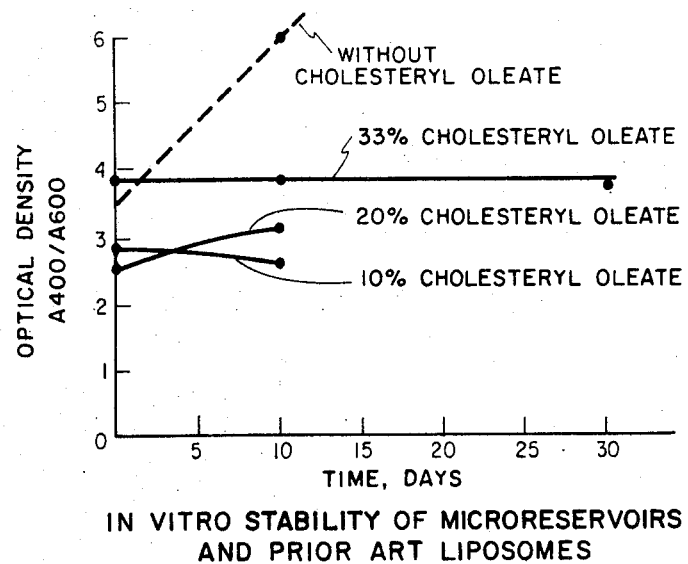
FIG. 6 illustrates the in vitro stability of the microreservoirs contrasted with that of liposomes, the in vitro stability being measured as the optical density of the microreservoirs and of the liposomes as a function of time.

The greatly enhanced in vitro stability of the microreservoirs of this invention compared with that of the liposomes suggested in the prior art is illustrated in Example 1 and FIG. 6.

EXAMPLE 1

Various mixtures of 60 μmoles of egg yolk phosphatidyl choline, various amounts of cholesteryl oleate and 4 mg of daunomycin, used as an exemplary xenobiotic, were taken to dryness under vacuum from a chloroform solution of these microreservoir constituents. To the resulting residue were added 5 ml of 0.1 M KCl and 10 mM of trihydroxymethylamine (buffer of pH 8.0); and the resulting suspension was sonicated at 120 watts for 15-minutes at 51° C. under a nitrogen atmosphere. Both of the suspensions were then spun at 100,000 g for one hour to remove any undispersed lipid.

Thin layer chromatograms of the centrifugates showed no evidence of degradation of the phosphatidyl choline or daunomycin. Aliquots of 4 ml of each sample were then placed into stoppered curvettes and the samples were incubated at 37° C. At various points in time optical densities of the two solutions at 400 nm and 600 nm were determined. The data thus obtained are plotted in FIG. 6 as the ratio of these optical densities, A400/A600, against time. Since both structures initially had essentially the same molecular size, the ratio of A400/A600 is an indication of any increase in the particle size due to the breakdown of the structural organization of the liposome.

FIG. 6 illustrates the dramatic difference in stability between the microreservoirs of this invention and similarly-sized liposomes. Whereas the absorbence of the microreservoirs containing 33% cholesteryl oleate, as well as lesser amounts of the cholesterol ester, was relatively stable, that of the liposome increased rapidly from the beginning of the period of evaluation and by the end of 10 days the liposome had degraded beyond all practical use. As previously, postulated, the marked degradation of the liposomes is believed to be due to the interaction with the aqueous environment and aggregation into larger particles, two factors absent in the microreservoirs by virtue of their structural stability and apolarity.

In addition to in vitro stability, the microreservoirs of this invention also exhibit a greatly increased in vivo stability over the liposomes. This is shown in Example 2 and FIG. 7.

EXAMPLE 2

100 μmoles of egg yolk phosphatidyl choline, 10 μmoles of $^{14}C$-labeled cholesteryl oleate and 10 μmoles of egg yolk phosphatidic acid were dissolved in chloroform and the solution evaporated in vacuo to dryness. 5 ml of 0.154 M NaCl and 10 mM of trihydroxymethylamine (pH 8.0) were added to the dry mixed lipid residue. The resulting suspension was sonicated for 15 minutes at 51° C. under a nitrogen atmosphere. The sonicated mixture was then chromatographed on a 2.5×40 cm Sepharose 4B column. Individual fractions that demonstrated a coincidence in the elution profile of the phospholipids and cholesteryl oleate were pooled and then concentrated by ultrafilatration. 1.1 ml of these concentrated microreservoirs were injected into the tail vein of a rat. Plasma samples were withdrawn at various time periods and assayed for the radioactivity associated with the microreservoirs contained in the plasma sample. The data thus obtained are plotted in FIG. 7 as a function of time after injection.

Figure 7:
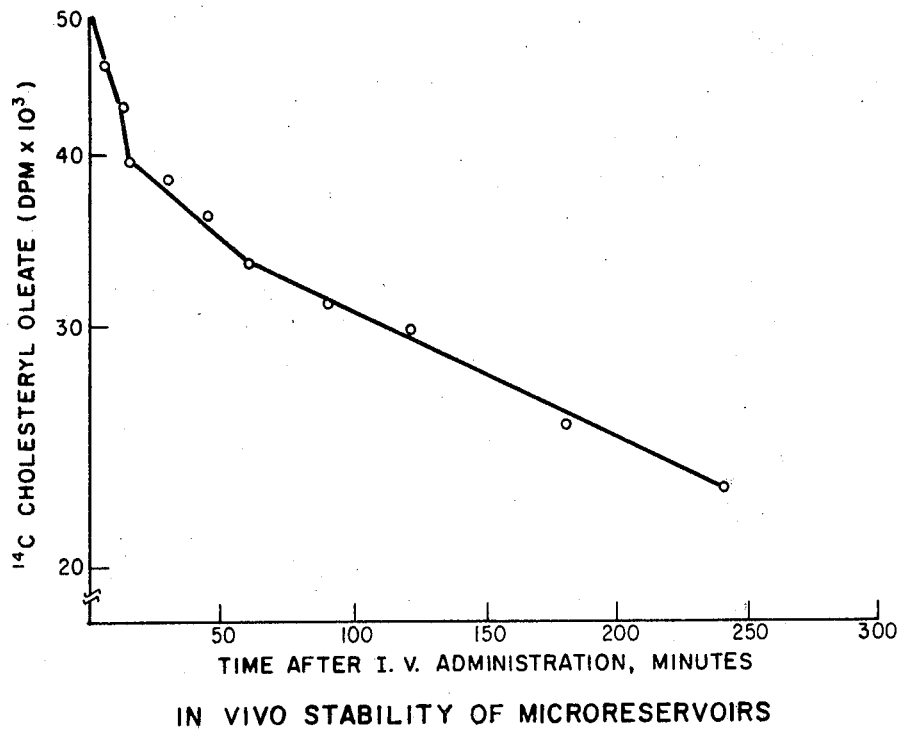
FIG. 7 illustrates the in vivo stability of the microreservoirs plotted as the amount of cholesteryl oleate (cholesterol ester) remaining in the blood plasma of a rat as a function of time.

Although the kinetics are complex, it can be seen from FIG. 7 that at equilibrium, the clearance of the microreservoirs has a half-life of 5.5 hours. In contrast, sonicated liposomes containing a similar negative charge have a plasma half-life of only 8 minutes. (R. L. Juliano and D. Stamp, *Biochem Biophys. Res Comm* 63: 651 [1975].) It seems logical to postulate that the nearly 40-fold increase in the lifetime achieved by the microreservoirs is attributable to increased structural stability.

In the following Examples 3-16, three well-known chemotherapeutic agents recognized as being capable of selectively blocking the multiplication of the neoplastic cells, e.g., those associated with various types of cancer, are employed as xenobiotics in forming exemplary xenobiotic delivery vehicles in accordance with this invention. The chemotherapeutic agents used in these examples are daunomycin (sometimes referred to as daunorubicin), adriamycin (also called doxorubicin) and AD 32. These compounds, along with a number of others including, for example, carminomycin, rhodomycin B, and the like, make up the class of so-called anthracycline antibiotics derived directly from the aerobic fermentation of *Streptomyces peucetius* and its variants or synthesized from such antibiotics so derived.

Daunomycin has been determined to have the following structural formula

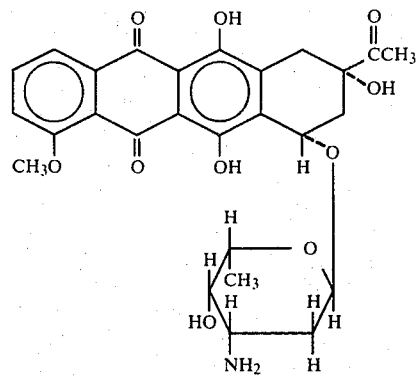

It has found use primarily in the treatment of acute myelogenous leukemia (DiMarco, A., and Lenaz, L. "Daunomycin and Adriamycin" in: J. F. Holland and E. Frei, III (eds.), "Cancer Medicine" pp 826–835. Philadelphia; Lea and Febiger, (1973); and Tan, C., Tasaka, H., Yu, K. P., Murphy, L., and Karnofsky, D. A. "Daunomycin, an Antitumor Antibiotic in the Treatment of Neoplastic Disease (Clinical Evaluation with Special Reference to Childhood Leukemia)" Cancer, 20: 333–353, (1967)).

Adriamycin is a glycoside antibiotic whose structure is represented below

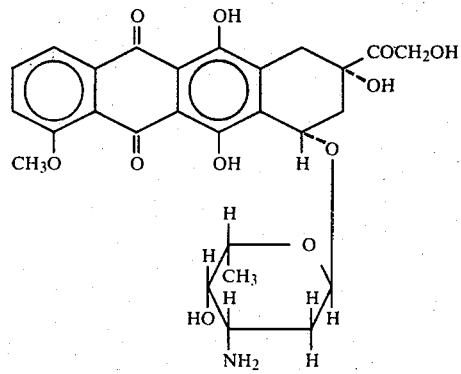

It is prepared either by aerobic fermentation of *Streptomyces peucetius* var. *caesius* followed by solvent extraction and chromatographic purification or by chemical synthesis from daunomycin (Arcamone, F., Barbieri, W., Franceschi, G., Penco, S.: *Chim. Ind.* (Milan) 51: 834 (1969).) Adriamycin is a commercially available antineoplastic agent which has found wide use, either alone or in combination, in the treatment of lymphatic leukemia, lymphomas, breast cancer, genitourinary tumors, epidermoid carcinomas, soft tissue sarcomas and bone sarcomas.

It has been widely investigated and used as is evident from the compilation "International Symposium on Adriamycin" edited by S. K. Carter, A. DiMarco, M. Ghione, I. H. Krakoff and G. Mathe, Springer-Verlag Berlin, Heidelberg, New York 1972.

AD 32, having the structure,

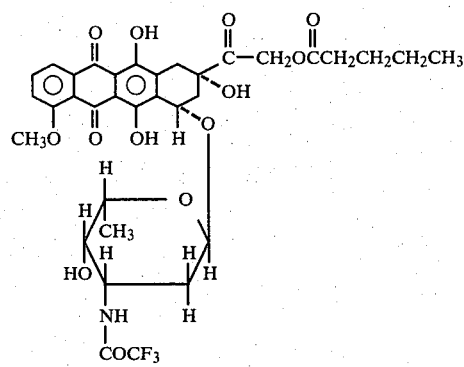

is synthesized from daunomycin. (Israel, M., Tinter, S. K., Lazarus, H., Brown, B., and Modest, E. J., "Adriamycin Derivatives: Preparations and Antitumor Evaluation Abstracts," Eleventh International Cancer Congress, Florence, Italy, October 1794, Vol. 4. pp 752–753). AD 32 has been found to exhibit significantly greater antitumor activity than adriamycin or daunomycin in two experimental mouse tumor systems, i.e., P388 leukemia system and L1210 leukemia system. (Israel, M. Modest, E. J., and Frei, Emil, III. "N-Trifluoroacetyladriamycin-14-Valerate, an Analog with Greater Experimental Antitumor Activity and Less Toxicity Than Adriamycin" *Cancer Research*, 35: 1365–1368 (May 1975).)

The effect that the incorporation of these antineoplastic agents into microreservoirs to form xenobiotic delivery vehicles has on their pharmacodynamics will be illustrated in the specific examples.

Figure 8:
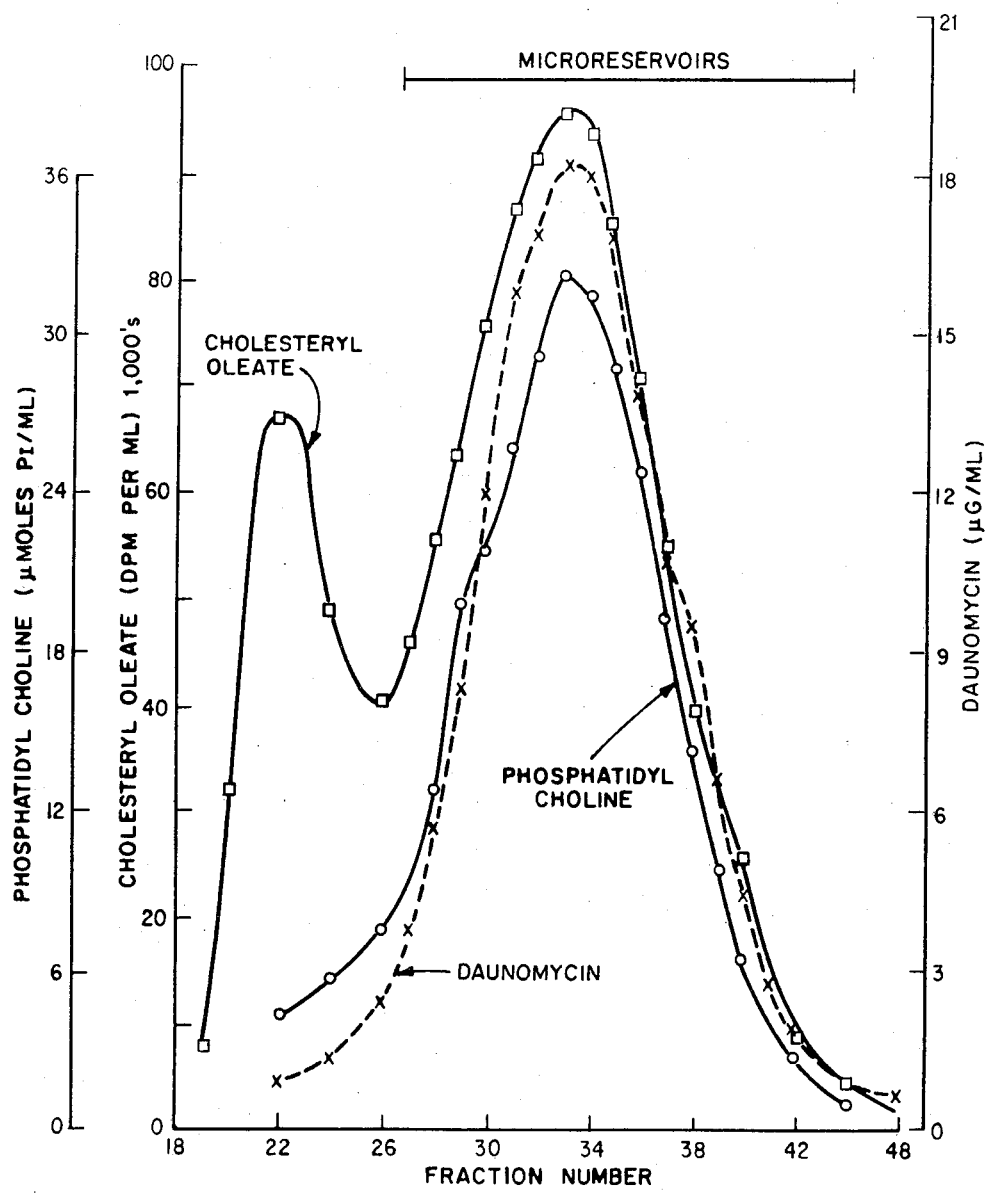
FIG. 8 is an elution profile of microreservoirs carrying daunomycin plotted as phosphatidyl choline, cholesteryl oleate and daunomycin concentrations in a series of chromatographic fractions.

The incorporation of a xenobiotic, represented by daunomycin, microreservoirs is illustrated in Example 3 and FIG. 8.

EXAMPLE 3

2180 μmoles of egg yolk phosphatidyl choline, 242 μmoles of cholesteryl oleate labeled with $^{14}C$ (specific activity $1.6 \times 10^4$ disintegrations per minute (dpm)/μmole and 36 mg of daunomycin were mixed together in chloroform and the solution was evaporated to dryness in vacuo. The mixed dry residue was then hydrated by the addition of 110 ml of 0.1 M KCl and 10 mM of trihydroxymethylamine (pH 8.0). This suspension was then sonicated with a Branson W-185 Sonifer for 15 minutes at 51° C. under a nitrogen atmosphere.

The sonicated liquid was then chromatographed on a 2.5×40 cm Sepharose 4B column. Individual fractions resulting from the chromatographing were then assayed for phosphatidyl choline content by the procedure of Gomori (*J. Lab. Clin. Med*, 27: 955 [1949]), for cholesteryl oleate by radioactivity and for daunomycin by fluorescence measurements. The results of these analyses are plotted in FIG. 8 with the analytical results for the cholesteryl oleate, phosphatidyl choline and daunomycin being superimposed.

The diameter of the vesicular microreservoirs was found to be approximately 200 Å to 300 Å as determined by their elution profile on the gel column which had previously been calibrated using sonicated liposomes of egg yolk phosphatidyl choline.

It can be seen from FIG. 8 that the elution profiles of the phosphatidyl choline (as monitored by phosphate analysis), of the cholesteryl oleate (as monitored by radioactivity) and of the daunomycin (as monitored by fluorescence) coincide, indicating that the xenobiotic (daunomycin) was associated with the vesicular microreservoirs. Since daunomycin is a relatively hydrophobic drug, with some hydrophilic characteristics, it is reasonable to postulate that the site of localization of the drug is within the lipid organization of the microreservoirs.

Figure 9:
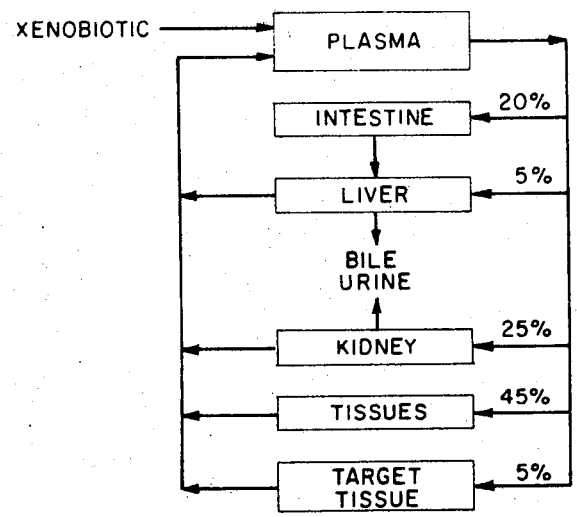
FIG. 9 is a diagrammatic representation illustrating the distrubution of a typical anthracycline drug shortly after injecting the free drug, showing how little of the drug remains in the blood stream for delivery to the target site.

Among the pharmacodynamics of a xenobiotic which can be altered to make the xenobiotic more effective are plasma kinetics, degree of toxicity and therapeutical effectiveness. Daunomycin is being clinically evaluated as a cancer chemotherapeutic drug; but it is relatively hydrophobic and it is very difficult to maintain in the plasma stream as evidenced by the fact that within two minutes after administration about 95% of it has left the bloodstream and gone to various organs leaving only some 5% to reach the target tissue, i.e., a tumor. This is illustrated in FIG. 9 which illustrates the distribution of a typical anthracycline drug, given intravenously, minutes after injection. Finally, daunomycin is known to be toxic, particularly since it tends to concentrate in the heart tissues, making it necessary not only to carefully monitor its administration but to administer it at very low dosage levels.

Figure 10:
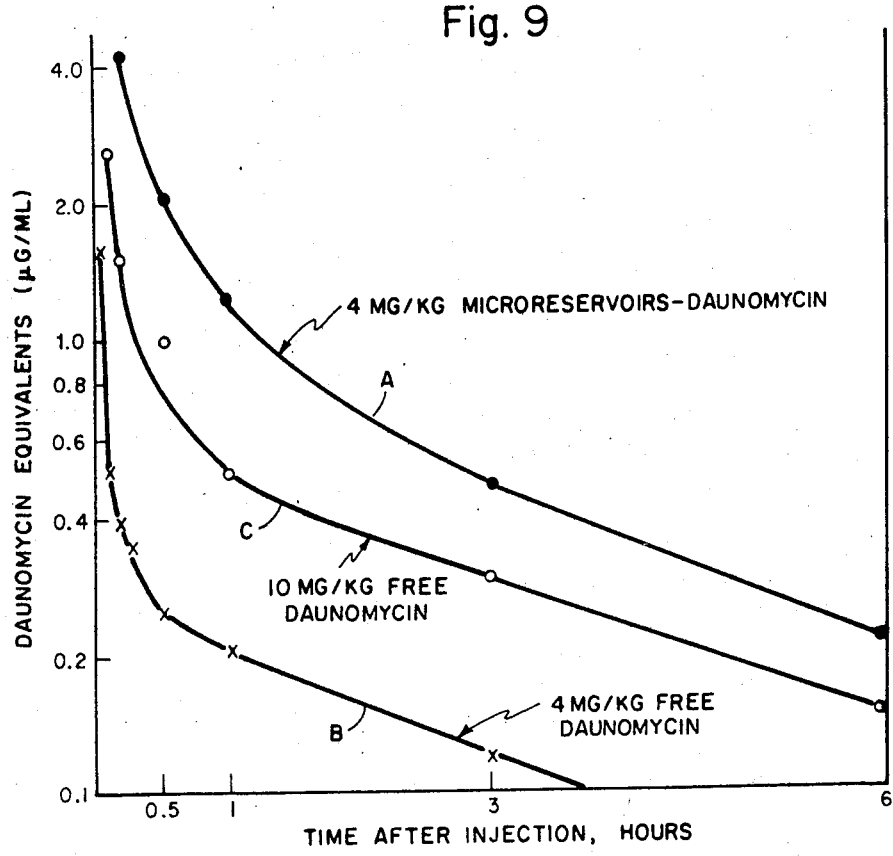
FIG. 10 illustrates the extent to which the circulating microreservoirs are capable of beneficially altering the plasma kinetics of daunomycin, the illustration being in the form of plots of the amount of daunomycin remaining in the bloodstream as a function of time after injection of the drug in the microreservoirs and as free daunomycin.
Figure 11:
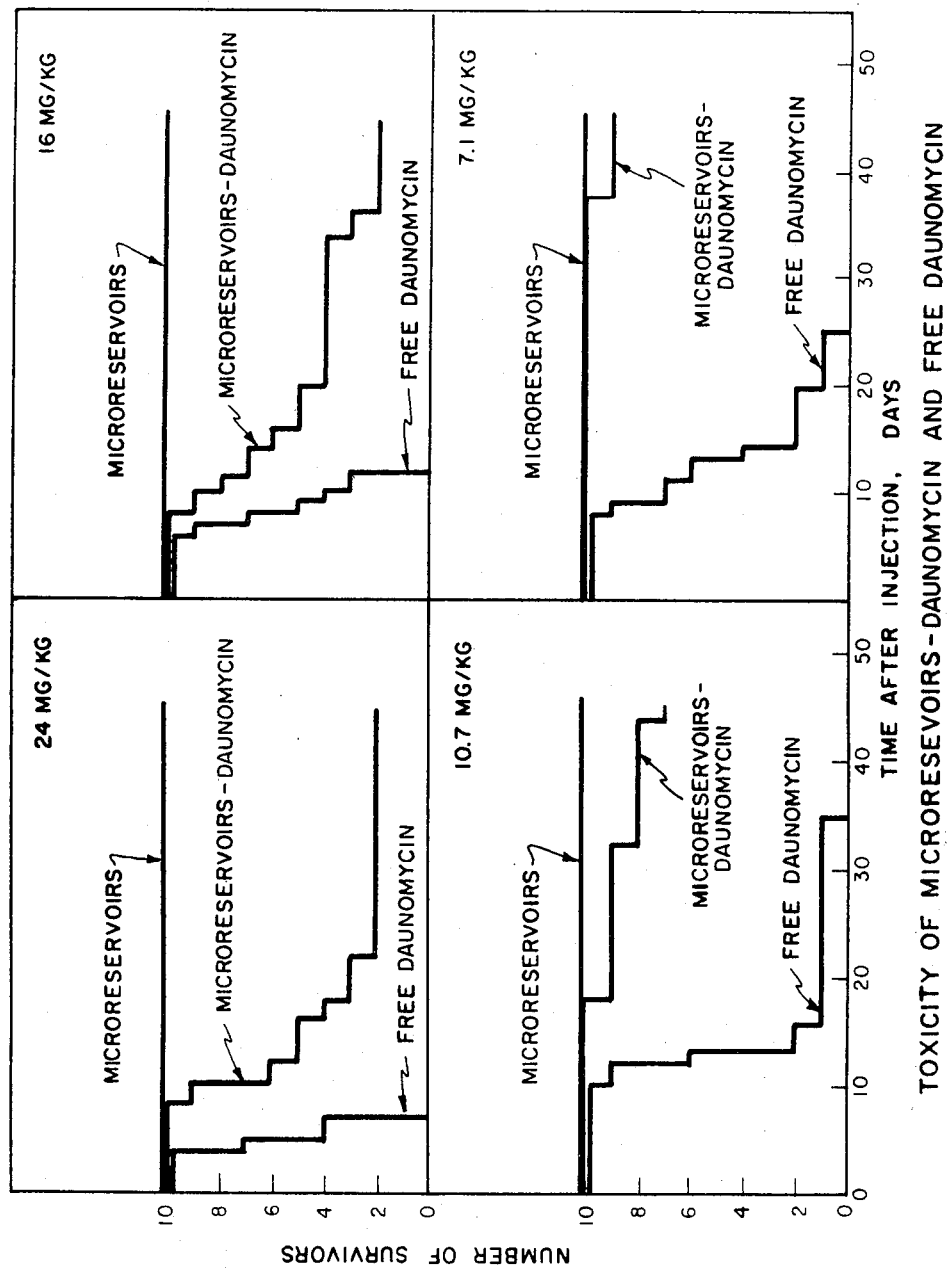
FIG. 11 is a series of plots of the number of survivors of a group of mice as a function of time after the injection at four dose levels of microreservoirs, daunomycin in the microreservoirs and daunomycin in free form, the plots illustrating the ability of the microreservoirs acting as delivery vehicles to decrease the toxicity of the daunomycin.
Figure 12:
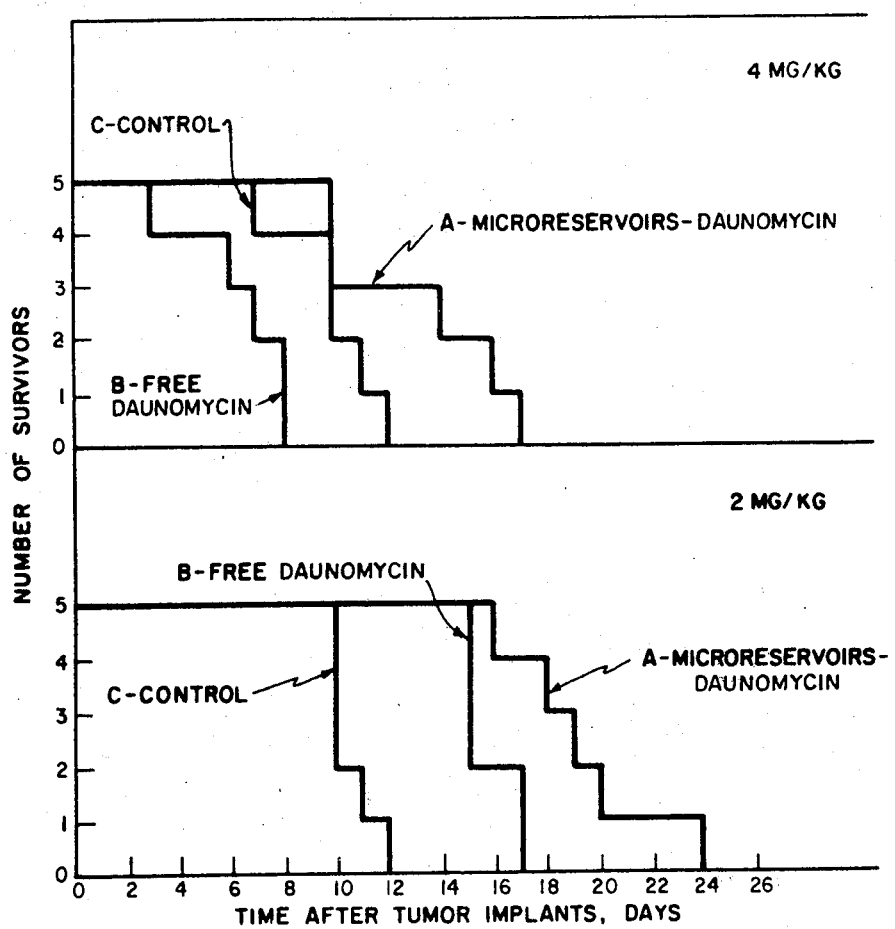
FIG. 12 is a series of plots of the number of survivors of a group of mice injected with tumor cells as a function of time after the injection at two dose levels of daunomycin in the microreservoirs and in free form, the plots illustrating the beneficial altering of the chemotherapy of the daunomycin delivered by and released from the microreservoirs.

The following Examples 4–6 and FIGS. 10–12 illustrate the ability of the microreservoirs of this invention circulating in the bloodstream to alter the plasma kinetics, toxicity and chemotherapeutical effectiveness of daunomycin.

EXAMPLE 4

200 μmoles of egg yolk phosphatidyl choline, 20 μmoles of cholesteryl oleate and 4 mg of daunomycin were dissolved in chloroform and then taken to dryness under vacuum. To the resulting dry residue were then added 5 ml of 0.154 M NaCl and 10 mM of trihydroxymethylamine (pH 7.4). This aqueous suspension was then sonicated for 15 minutes at 51° C. under a nitrogen atmosphere. The daunomycin which was not contained within the vesicular microreservoirs formed was separated from the microreservoirs by passage through a 2.5×20 cm Sephadex G-50 gel column. The void volume which contained the daunomycin incorporated in the microreservoirs was concentrated to 3 mg daunomycin/ml.

A control sample of free daunomycin at the same concentration and in the same buffer was also prepared.

Three rats were injected intravenously with the microreservoirs containing daunomycin; and six other rats were injected intravenously with the free daunomycin. The dosage of the daunomycin contained within the microreservoirs was 4 mg/kg; and that for the free daunomycin was 4 mg/kg in three rats and 10 mg/kg in the remaining three rats. 0.5 ml of blood was taken at various time points from each rat. The plasma was separated from the blood samples and assayed for daunomycin fusing fluorescence. The data thus obtained are plotted in FIG. 10 as a function of time after injection.

It is apparent from FIG. 10 that the use of circulating microreservoirs as a delivery vehicle for the daunomycin beneficially alters and improves the plasma kinetics for that drug. From a comparison of Curves A and B, representing the same dosage level, it will be seen that after about 15 minutes the concentration of daunomycin in the circulating microreservoirs in the plasma was about 4 μg/ml; while the concentration of the free daunomycin in the plasma was about 0.4 μg/ml. Therefore, at this time point, the concentration of daunomycin in the bloodstream carried by the circulating microreservoirs was some ten times greater than when this drug was introduced directly into the bloodstream. Furthermore, it will be seen from FIG. 10, the free daunomycin was virtually absent from the bloodstream after some $3\frac{3}{4}$ hours; while it was still up to a concentrtion of about 0.4 μg/ml in the circulating microreservoirs at this time point. Thus the concentration of the drug in the bloodstream carried in the circulating microreservoirs after $3\frac{3}{4}$ hours was equivalent to that after only 15 minutes when the drug was introduced in the free form.

A further comparison of Curve A with Curve C (free daunomycin in a dosage of 10 mg/kg) shows that after one hour the concentration of the drug in the plasma was about 1.3 μg/ml when carried by the circulating microreservoirs and about 0.5 μg/ml when in free form; after 3 hours these figures were about 0.5 μg/ml and about 0.3 μg/ml; and after 6 hours they were about 0.21 μg/ml and about 0.14 μg/ml, respectively. Thus, the use of the circulating microreservoirs of this invention can provide concentrations of this drug in the bloodstream which are materially greater than those achieved when the same drug is administered in free form in dosages 2.5 times greater than when administered through the microreservoirs.

The altering of the plasma kinetics of a drug such as daunomycin, and as illustrated in FIG. 10, means that it has a less toxic effect since it is maintained within the bloodstream longer and is thus prevented from concentrating in such organs as the liver, kidney and heart. It also means that any given dosage is more effective when carried by the circulating microreservoirs than when circulating freely, since the more drug that remains in the bloodstream the more exposure there will be of the target tissue to the daunomycin dose. Since the effectiveness of this drug in killing tumor cells is based upon the ability of the tumor cells to take it up, maximum contact between the drug and cells is essential for maximum effectiveness.

Finally, altering of the plasma kinetics of a xenobiotic as shown in FIG. 10 offers the possibility of decreasing dosages; for if the performance of, say, the 10 mg/kg dose of Curve C could be considered adequate for chemotherapeutical purposes, it becomes apparent that the dosage level could be reduced below 4 mg/kg if the drug is delivered and released from the circulating microreservoirs. Such a decrease in dosage would also materially reduce toxicity.

That a marked reduction in daunomycin toxicity is achieved through the use of the circulating microreservoirs is shown in Example 5 and FIG. 11.

EXAMPLE 5

1000 μmoles of egg yolk phosphatidyl choline, 100 μmoles of cholesteryl oleate and 20 mg of daunomycin were dissolved in chloroform and the solution was taken to dryness in vacuo. To the resulting dry residue mixture were added 20 ml of 0.1 M KCl and 10 mM of trihydroxymethylamine (pH 8.0). The aqueous suspension was sonicated for 15 minutes at 51° C. under a nitrogen atmosphere. The sonicated liquid was chromatographed on a 2.5×40 cm Sepharose 4B gel column. Only those fractions which showed a coincidence of the elution profile of phosphatidyl choline, cholesteryl oleate and daunomycin were pooled. These pooled fractions were then concentrated by ultrafiltration, using an XM-50 membrane, to a final concentration of 3 mg of daunomycin per ml.

A similar sample of microreservoirs without daunomycin was also prepared and concentrated to the same microreservoir concentration. A solution of free daunomycin at a concentration of 3 mg/ml in 0.1 M KCl and 10 mM of trihydroxymethylamine (pH 8.0) was also prepared as a control to be used as free daunomycin.

The microreservoirs containing the daunomycin, the microreservoirs without the drug, and the free drug were injected at various drug doses into mice, using a single intraperitoneal injection. Ten $BDF_1$ mice were used for each protocol; and the resulting data are plotted in FIG. 11. These plots show the survival rate of the mice as a function of time. It will be seen that the microreservoirs themselves, in the absence of daunomycin, exhibited no toxicity. At all of the dosage levels, the use of the circulating microreservoirs to carry the daunomycin decreased the toxic effects of the drug compared to that exhibited by the free daunomycin. As the dosage levels decreased the ability of the delivery vehicles to reduce toxicity became more marked in comparison with the free drug. It is believed that this reduction in toxicity can be explained, at least in part, by the ability of the circulating microreservoirs to keep the daunomycin in the bloodstream and out of the tissues and organs, particularly the heart.

The effect of the chemotherapy of daunomycin using the delivery vehicles of this invention is illustrated in Example 6 and FIG. 12.

EXAMPLE 6

The procedures of Example 5 were followed to make vesicular microreservoirs with and without daunomycin and to prepare daunomycin for use as a free drug. A number of mice were injected intraperitoneally with $1 \times 10^6$ P388 tumor cells. Twenty-four hours later single daily intraperitoneal doses of the vesicular microreservoirs with and without daunomycin and free daunomycin were injected for a period of 5 days after the tumor implants. One group of mice, used as a control, received no drug in any form. Five mice were used for each protocol and two different dosage levels, 4 mg/kg and 2 mg/kg, were used. The data obtained from these tests are plotted in FIG. 12 as number of survivors as a function of time.

The mice injected with the microreservoirs without daunomycin had a survival rate (not plotted) similar to that of the control mice, Curves C in the plots. At the dosage level of 4 mg/kg the daunomycin delivered by the circulating microreservoirs exhibited chemotherapeutic effect while the free drug at the same dosage level demonstrated a toxicity measurably greater than the tumor cells. At the lower dosage level of 2 mg/kg, the daunomycin delivered by the circulating microreservoirs exhibited a greater chemotherapeutic response than the free drug.

In formulating the microreservoirs of this invention, it may be desirable to include one or more xenobiotic binding modifiers which are capable of either increasing or decreasing the relative amount of the xenobiotic picked up by the microreservoirs during their formation. For example, it has been found that a minor mole percent, i.e., about 5 mole percent or more, of phosphatidic acid, a charged lipid, added to the phospholip constituent of the microreservoirs may increase the affinity of the xenobiotic for the microreservoirs. It is, therefore, within the scope of this invention to use one or more different phospholipids to make up the phospholipid constituent of the microreservoir composition. It is, moreover, within the skill of the art to choose a single phospholipid or an optimum combination of phospholipids as the phospholipid constituent of the microreservoirs to obtain a predetermined pickup of the xenobiotic.

It is also possible to modify the binding of a xenobiotic to the reservoir by the inclusion of other lipids which are soluble in the phospholipid constituent or slightly soluble in the cholesterol ester or triglyercide constituent. The modifications achieved in a microreservoir/daunomycin system are illustrated in Example 7 and Table 1; and the effect such modifications have on the xenobiotic efflux or release rates of the resulting microreservoirs is illustrated in Example 8 and FIGS. 13 and 14.

EXAMPLE 7

A series of formulations of microreservoirs containing 105 μmole of $^{14}$C-labeled egg yolk phosphatidyl choline (specific activity 4160 dpm/μmole phosphatidyl choline), 11.6 μmoles of cholesteryl oleate, or 11.6 μmoles of triolein (glyceryl trioleate), with or without a second phospholipid as represented by 11.6 μmoles of phosphatidic acid, and with or without cholesterol as a modifying agent present in an amount from 0 to 75 μmoles was made up. In each formulation, 1.72 mg of daunomycin was used as the xenobiotic to be carried and released.

The formulations were prepared as solutions of chloroform which were taken to dryness in 10-ml screw-cap vials and pumped overnight. Each formulation sample was then hydrated with 3 ml of 0.154 M NaCl and 10 mM of trihydroxymethylamine (pH 7.2) and then vortexed for several minutes at room temperature. Each sample was then sonicated at the appropriate temperature for 20 minutes in a stream of nitrogen. Sonication of those samples containing cholesteryl oleate was carried out at 51° C.; and of those containing triolein at 3° C. After sonication, each sample was spun in a desktop centrifuge for 10 minutes to remove any titanium fragments.

Each sample was passed down a 2.5×15 cm Sephadex G-50 column using 0.154 M NaCl and 10 mM trihydroxymethylamine as the eluting buffer. The void volume of each of the G-50 columns, which contained the microreservoirs, was collected and assayed for $^{14}$C egg yolk phosphatidyl choline radioactivity and for the fluorescence from the daunomycin. The results of these measurements in terms of μg daunomycin/μmole phosphatidyl choline and μg daunomycin/μmole total phospholipid and the percent of daunomycin pick up by the microreservoirs are tabulated in Table 1.

In reporting these results, the percent daunomycin encapsulated was normalized to the sample that had the highest degree of encapsulated daunomycin per μmole of total phospholipid.

TABLE 1
EFFECT OF COMPOSITION OF PHOSPHOLIPID CONSTITUENT AND OF THE ADDITION OF PHOSPHOLIPID-MISCIBLE LIPIDS ON THE PICKUP OF DAUNOMYCIN BY MICRORESERVOIRS

| Sample No. | Microreservoir Composition Mole% | | | | | μg Daunomycin/ | | % Encapsulated |
|---|---|---|---|---|---|---|---|---|
| | PC | GTO | CO | PA | Chol | μmole PC | μ mole PL | |
| 1 | 82 | 9 | — | 9 | — | 6.67 | 6.03 | 100 |
| 2 | 90 | 10 | — | — | — | 4.90 | 4.90 | 81 |
| 3 | 82 | 9 | — | — | 9 | 4.26 | | 71 |
| 4 | 72 | 8 | — | — | 20 | 4.14 | 4.14 | 69 |
| 5 | 65 | 7 | — | — | 28 | 4.03 | 4.03 | 67 |
| 6 | 54 | 6 | — | — | 40 | 3.91 | 3.91 | 65 |
| 7 | 82 | — | — | 9 | — | 5.83 | 5.27 | 87 |
| 8 | 90 | — | 10 | — | — | 4.41 | 4.41 | 73 |
| 9 | 82 | — | 9 | — | 9 | 4.21 | 4.21 | 70 |
| 10 | 72 | — | 8 | — | 20 | 3.43 | 3.43 | 57 |
| 11 | 65 | — | 7 | — | 28 | 3.14 | 3.14 | 52 |
| 12 | 54 | — | 6 | — | 40 | 2.36 | 2.36 | 40 |

PC - Phosphatidyl choline
GTO - Glycerol trioleate
CO - Cholesteryl oleate
PA - Phosphatidic acid
Chol - Cholesterol
PL - Total phospholipids (PC and PA)

From the data in Table 1 it will be seen that the inclusion of a small amount of phosphatidic acid in the phospholipid constituent (Samples 1 and 7) increased the uptake of daunomycin by the microreservoirs. In contrast to imidocarb, (examples 13–15) which requires the inclusion of phosphatic acid, daunomycin, which has an ionizable amine functional group profits from the use of phosphatidic acid as a portion of the phospholipid constituent. Thus phosphatidic acid is seen to be applicable to xenobiotics of varying characteristics.

The incorporation of cholesterol, a phospholipidmiscible lipid, in the microreservoir composition inhibited the binding of the daunomycin to the microreservoirs. The addition of cholesterol to microreservoir compositions containing glycerol trioleate (Samples 3–6) had a markedly less effect on the binding of the drug than in the case where the microreservoir composition contained cholesteryl oleate (Samples 9–12). Finally, the data of Table 1 indicate that in the case of daunomycin the use of glycerol trioleate (Samples 1–6) in place of cholesteryl oleate (Samples 7–12) facilitates the binding of this xenobiotic to the microreservoirs. It is therefore apparent that through the choice of the phospholipid constituent and the phospholipid-immiscible constituent (with or without an additional xenobiotic binding modifier) it is possible to control and predetermine the degree of xenobiotic uptake in or binding to the microreservoirs. Such control offers flexibility in the xenobiotic delivery system of this invention with respect to dosage levels, rate of xenobiotic release, and the like.

Not only can the equilibrium binding of a xenobiotic be affected by the microreservoir composition, but also the efflux or release rate of the xenobiotic can be controlled and predetermined by the composition. This is illustrated through the use of a model system which permitted the determination of xenobiotic efflux rates from the microreservoirs in response to nonequilibrium conditions as detailed in Example 8 and shown in FIGS. 13 and 14.

EXAMPLE 8

Microreservoirs were formulated as described in Example 7. To establish the required nonequilibrium conditions the microreservoirs containing daunomycin as the xenobiotic were incubated with a large excess of unsonicated egg yolk phosphatidyl choline dispersions. These dispersions were formed by adding aliquots of microreservoirs of the various compositions containing approximately 1 $\mu$mole of egg yolk phosphatidyl choline to 9 $\mu$moles of unsonicated egg yolk phosphatidyl choline in 1.0 ml of 0.154 M NaCl and 10 mM of trihydroxymethylamine (pH 7.2). Comparable control dispersions were made up to contain an equivalent amount of free daunomycin in place of that carried by the microreservoirs.

In assessing the efflux rate of the daunomycin, one of the mixtures thus formed was used for each time point. At the designated time, the sample was centrifuged at 15,000 g for 2 minutes under which conditions the unsonicated dispersion was readily separated from the microreservoirs remaining in the resulting supernatant. Since the daunomycin tends to re-equilibrate between the microreservoirs and the unsonicated phospholipid dispersions, the rate of equilibrium can be used as a kinetic parameter to evaluate the role of various constituents forming the microreservoir composition in determining the efflux rate of the daunomycin contained in the microreservoirs.

An aliquot of the resulting supernatant was assayed for fluorescence and the amount of fluorescence thus remaining was compared with that initially present in the mixture. This amount of daunomycin remaining in the supernatant therefore represents the amount of the drug still contained in the microreservoirs.

The data obtained from this series of measurements are plotted in FIGS. 13 and 14 which show decrease of fluorescence as a function of time for the microreservoirs containing glycerol trioleate (FIG. 13) and cholesteryl oleate (FIG. 14). From the data plotted in FIGS. 13 and 14 it will be seen that the free daunomycin was very rapidly removed from the supernatant, whereas that bound to the microreservoirs was retained to a much greater degree. The inclusion of 9 mole % of phosphatidic acid in the phospholipid constituent of the microreservoirs materially retarded the efflux rate, while the addition of cholesterol increased it. Finally, the use of a triglyceride in place of a cholesterol ester slightly decreased the efflux rate.

These kinetic evaluations based on efflux rates contribute to the significance of the data of Table 1 concerning the equilibrium binding of daunomycin to the microreservoirs; and these data confirm the fact that the composition of the microreservoirs can be chosen to predetermine and control the pharmacodynamics of the xenobiotic contained in the microreservoirs serving as the drug delivery vehicle of this invention.

Adriamycin is at present among the most widely used of all antineoplastic agents. It is water soluble and a positively charged molecule which does not bind as strongly to the microreservoirs as does, for example, daunomycin. However, by increasing the negative charge on the microreservoirs, such as by using phosphatidic acid as one component of the phospholipid constituent, it is possible to materially increase the amount of adriamycin to and carried by the microreservoirs. This is illustrated in Example 9 and FIG. 15.

EXAMPLE 9

For each sample, the total lipid constituent consisted of 80 $\mu$moles of total phospholipid (soybean phosphatidyl choline and phosphatidic acid) and 20 $\mu$moles of cholestryl oleate. With this 2 mg (3.45 $\mu$moles) of adriamycin was used. In the five samples, the amount of phosphatidic acid in the total lipid constituent was varied from zero to 25%. The phospholipids, cholesteryl oleate and adriamycin were dissolved in chloroform and the solution was taken to dryness in vacuo. To each dry sample were then added 6 ml of 0.15 M NaCl and 10 mM of trihydroxymethylamine (pH 7.2). The aqueous suspensions were each sonicated at 52° C. for 15 minutes. Each sample was passed down through a 2.5×50 cm Sephadex G-50 gel column to separate free and bound adriamycin.

In FIG. 15 the $\mu$moles of bound adriamycin are plotted against the amount of phosphatic acid in the total lipids. It will be seen that this amount of bound adriamycin increases with increasing amounts of phosphatidic acid, relative to total lipids, up to about 25 mole % and then levels off.

Using the data obtained in Example 9 as a guide to obtaining the maximum binding of adriamycin within the reservoirs, adriamycin-containing microreservoirs were formulated and the effects of using the microreservoirs to carry and release the adriamycin on toxicity and chemotherapeutic activity and the drug were determined. Examples 10–12 and FIGS. 16 and 17 give these data.

EXAMPLE 10

2875 $\mu$moles of purified soybean phosphatidyl chloine (specific activity 2296 $^3$H dpm/$\mu$mole) 720 $\mu$moles of soybean phosphatidic acid and 720 $\mu$moles of cholesteryl oleate (specific activity of 3638 $^{14}$C dpm/$\mu$mole) were dissolved in choloroform and taken to dryness by pumping overnight against a vacuum. The resulting solid material was hydrated with 20 ml of 10 mM of trihydroxymethylamine (pH 9.1) and the liquid was sonicated at 52° C. under a nitrogen atmosphere for 15 minutes. The pH of the solution was lowered to 7.2 and then it was centrifuged for one hour at 100,000 g. 34.9 mg of adriamycin was added to the clear supernatant and it was then allowed to incubate for 30 minutes at room temperature. After this incubation, the ionic strength of the solution was increased to 0.154 M NaCl; and it was passed down a 4.3×37 cm G-50 Sephadex G-50 column using 0.154 M NaCl and 10 mM trihydroxymethylamine as the eluting solvent. Analysis of the resulting adriamycin-containing microreservoirs showed that somewhat more than 90% of the adriamycin originally added was incorporated into the microreservoirs. The microreservoirs were concentrated by ultrafiltration for evelation of toxicity and chemotherapy.

EXAMPLE 11

To determine the effect which the incorporation of adriamycin in the microreservoirs has on the toxicity of this drug, mice were given intraperitoneal injections of the microreservoir-adriamycin prepared in Example 10 and of free adriamycin. Two dosages levels of the drug were chosen—4 mg/kg and 2 mg/kg. In each case, six normal mice received the injections each day for five days and then they were observed thereafter to determine the number of survivors. The results are plotted in FIG. 16.

As shown in FIG. 16, at the dosage level of 4 mg/kg the free adriamycin proved highly toxic as evidenced by the survival of only one mouse at the end of 30 days. In direct contrast to this, all six mice survived through 30 days when given the same adriamycin dosage in the microreservoirs. At the lower dosage levels, none of the mice succumbed to the adriamycin within thirty days.

From these data it will be seen that the drug delivery system of this invention benefits the pharmacodynamics of adriamycin in that it reduces or prevents the toxic effects normally associated with this widely used antineoplastic agent. Given this marked decrease in toxicity, the next determination to be made is the effect that delivering and releasing the adriamycin from the microreservoirs has on its chemotherapeutic ability. This is shown in Example 12 and FIG. 17.

EXAMPLE 12

72 normal mice were each innoculated with $10^6$ L1210 leukemic cells by intraperitoneal injection on day zero. The 72 mice were divided into four dosage groups of 18 each; and in each group 6 control mice received no drug, 6 received the prescribed dosage as free adriamycin and 6 received the same dosage of adriamycin in the microreservoirs as prepared in Example 10. The drug in all cases was also given by intraperitoneal injection and the dosages were repeated daily on days 1 through 5. The dosage levels chosen were 4 mg/kg, 2 mg/kg, 1 mg/kg and 0.5 mg/kg. The animals were then observed daily to determine the number of survivors in each group and the results are plotted in FIG. 17.

In the group receiving the largest dosage—4 mg/kg—the adriamycin given in the free form was apparently able to exercise some therapeutic effect for a short period of time; but by day 24 all of the control mice and those receiving the free adriamycin had succumbed to leukemia and/or the toxic effect of the drug. However, those animals receiving the adriamycin in the microreservoirs were better able to combat the combined effect of the tumor cells and the adriamycin; for at day 30, two mice were still surviving. At the lower dose levels, the free adriamycin and that carried in the microreservoirs showed essentially equivalent chemotherapeutic activity.

From these data it may be concluded that the delivery of adriamycin from microreservoirs does not antagonize its chemotherapy. Furthermore, it seems probable that the long-term survivors receiving adriamycin dosages of 4 mg/kg from the microreservoirs are indicative of an increase in the therapeutic index of the drug which is accompanied by a decrease in its toxicity.

AD 32 is a highly hydrophobic analog of adriamycin used in chemotherapy. Since this drug is totally insoluble in an aqueous buffer, it is necessary to use a combination of a detergent and an organic liquid to form a solution of AD 32 suitable for clinical use. Exemplary of one such solvent presently in use is a mixture of equal volumes of ethanol and a sulfated ethylene glycol detergent (emulphol).

In spite of the hydrophobic nature of AD 32, it is possible to incorporate it into the microreservoirs in accordance with this invention and thus to beneficially alter its pharmacodynamics with respect to both plasma kinetics and therapeutic effectiveness as illustrated in Examples 13-16 and FIGS. 18-21.

EXAMPLE 13

1090 μmoles of phosphatidyl choline derived from egg yolk, 121 μmoles of $^3$H-labeled cholesteryl oleate (specific activity of 190,000 dpm/μmole) and 17.5 mg of AD 32 were dissolved in chloroform, then taken to dryness and pumped overnight. 5.5 ml of 0.154 M NaCl and 5 mM of trihydroxymethylamine (pH 7.41) were added to the dry mixture. The liquid was sonicated at 48° C. under a nitrogen atmosphere and the resulting sonicated liquid was chromatographed on a 2.5×40 cm Sepharose 4B column. Individual fractions thus obtained were assayed for phosphatidyl choline content, for cholesteryl oleate and for AD 32 as previously described. The elution profile, a composite of the assays, is plotted in FIG. 18. From this plot it can be seen that the AD 32 is associated with both nonvesicular microreservoirs (fractions 2–5) and vesicular microreservoirs (fractions 6–18).

The inclusion of a minor amount of phosphatidic acid in the phospholipid constituent of the microreservoir composition was found to have little, if any, effect on the efflux rate of AD 32 when a triglyceride was used as the phospholipid-immiscible constituent. This is evident from Example 14 and FIG. 19.

EXAMPLE 14

A basic microreservoir formulation containing 104.6 μmoles egg yolk phosphatidyl choline, and 11.6 μmoles of $^3$H-labelled glycerol trioleate (specific activity of $1.5\times10^5$ dpm/μmole) was used. 1.73 mg of AD 32 was added and in one formulation 11.62 μmoles of egg yolk phosphatidic acid was also added. These formulations were taken to dryness from a chloroform solution and pumped overnight under vacuum. 3 ml of 0.154 M NaCl and 10 mM trihydroxymethylamine were added to each sample and the hydrated liquids were sonicated for 20 minutes at 3° C. under a nitrogen atmosphere. Each sample was passed down a 2.5×20 cm Sephadex G-50 column and a quantity of each resulting vesicular microreservoir sample equivalent to one μmole of phospholipid was incubated with 9 μmoles of phosphatidyl choline liposomes in 0.46 ml of a buffered saline solution to form a dispersion.

At various time points, the resulting dispersions were centrifuged at 15,000 g for 2 minutes and the amount of fluorescence remaining in the supernatant was determined. The data from these measurements of efflux rate are plotted in FIG. 19. It will be seen that the efflux rate of AD 32 is relatively rapid and essentially unaffected by the inclusion of phosphatidic acid in the microreservoir composition.

Although the efflux rate of AD 32 from the microreservoirs is comparatively rapid, the use of microreservoirs bring about a marked beneficial alteration of the plasma kinetics of this drug, compared to the presently used dosage forms. This is illustrated in Example 15 and FIG. 20.

EXAMPLE 15

Fractions 6–18 of Example 13 were concentrated by ultrafiltration to an AD 32 concentration of 3.2 mg/ml. Sufficient quantities of the AD 32 in the microreservoirs were injected intravenously into 150-gram rats to provide a dosage level of 15 mg/kg; and a clinical formulation of AD 32 dissolved in a 1-to-1 by volume mixture of ethanol/emulphol was similarly injected at the same dosage level in three control rats. Plasma samples were taken at various points in time and AD 32 concentrations in these plasma samples were determined by fluorescence. The resulting data (average of three rats for each point) are plotted in FIG. 20 as AD 32 equivalents as a function of time from initial injection.

FIG. 20 shows the marked alteration in the plasma kinetics of AD 32 achieved through the use of the microreservoirs of this invention, for the levels of AD 32 in the plasma in which the drug was incorporated in microreservoirs were consistently higher by a factor of between 2 and 3 at all time points than for the free AD 32 introduced as the clinical solution. By allowing the drug a longer period of time to seek out tumor cells, this alteration in its plasma kinetics enhances its effectiveness as a chemotherapeutic agent. This is shown in Example 16 and FIG. FIG. 21.

EXAMPLE 16

Vesicular microreservoirs containing AD 32 were formulated as in Example 13 and concentrated to 3.2 mg AD 32/ml. A number of mice were injected intraperitoneally with $1 \times 10^6$ P388 tumor (leukemic) cells. Twenty-four hours later single daily intraperitoneal doses of the vesicular microreservoirs with AD 32 and saline control solutions were injected for a period of 5 days after the tumor implants. Five mice were used for each protocol and four different dosage levels, 7.3 mg/kg, 4 mg/kg, 2 mg/kg, and 1 mg/kg were used. The data obtained from these tests are plotted in FIG. 21 as number of survivors as a function of time. In all cases the mice injected with the microreservoirs containing AD 32 had a survival rate higher than that of the control mice. Moreover, even at the very low dosage level of 1 mg/kg the AD 32 delivered by the circulating microreservoirs exhibited chemotherapeutic effect and brought about a significant increase in survival of mice given the P388 leukemic cells.

As in the case of daunomycin, the same plasma concentrations of AD 32 can be achieved with lower initial levels of AD 32 carried by the microreservoirs than in clinical formulations. Furthermore, the microreservoir composition is more biocompatible with blood than the mixed solvent of ethanol and detergent now required in clinical formulations of AD 32.

The preceding examples illustrate the effectiveness of the delivery vehicle of this invention in beneficially altering the pharmacodynamics of the anthracycline class of chemotherapeutic agents. The microreservoirs of this invention may also be used to deliver other classes of chemotherapeutic agents including, for example, nitrosoureas and metabolites.

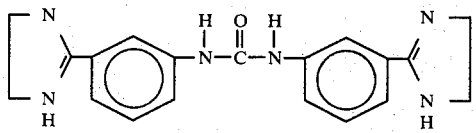

is a drug which has proven very effective as a parasiticide in the treatment of anaplasma in animals by killing parasites in the b bloodstream. However, when administered at its most effective dosage levels, traces of the imidocarb tend to remain in the animal tissue, an undesirable situation if the animal is to be used for human consumption. Therefore, it would be desirable to have a delivery vehicle capable of maintaining the imidocarb in the circulating bloodstream allowing it to perform its therapeutic function without accummulating in the animal tissue.

Imidocarb and its hydrochloric acid salt are hydrophilic compounds, a characteristics which differentiates them from the hydrophobic or hydrophobic/hydrophilic drugs. However, as will be seen from the following Examples 17 and 18, and FIGS. 22-24, the microreservoirs are equally effective in beneficially altering the pharmacodynamics of a hydrophilic xenobiotic such as imidocarb.

EXAMPLE 17

900 $\mu$moles of egg yolk phosphatidyl choline, 100 $\mu$moles of phosphatidic acid, 100 $\mu$moles of $^3$H-labeled cholesteryl oleate (specific activity $1.6 \times 10^4$ dpm/$\mu$mole) and 9.16 mg of $^{14}$C-labeled imidocarb were dissolved in chloroform and the solution was evaporated to dryness under vacuum. The resulting mixed dry residue was then hydrated by the addition of 45 ml of 0.154 M NaCl and 290 mM of trihydroxyethylamine (pH 8.0) to the mixed lipid/drug residue. The liquid was then sonicated for 15 minutes at 51° C. under a nitrogen atmosphere.

The sonicated liquid was then chromatographed on a $2.5 \times 40$ cm Sepharose 4B column. Individual fractions resulting from the chromatographing were then assayed for phosphatidyl choline and phosphatidic acid by the method of Gomori, and for the $^3$H-cholesteryl oleate and the $^{14}$C-imidocarb by radioactivity. The results of these analyses are plotted in FIG. 22 as a function of fraction number, the analytical results being superimposed as in FIG. 8. The diameter of the vesicular microreservoirs was found to range between about 200 Å and 300 Å.

It can be seen that the elution profiles of the three constituents of the microreservoirs coincide from fractions 5 through 9, indicating that the imidocarb was associated with the microreservoirs.

The beneficial alteration of the plasma kinetics of imidocarb attained through the use of the delivery vehicles of this invention is illustrated in Example 18 and FIGS. 23 and 24.

EXAMPLE 18

100 $\mu$moles of phosphatidyl choline and 10 $\mu$moles of phosphatidic acid derived from egg yolk, 10 $\mu$moles of cholesteryl oleate and 2 mg of $^{14}$C-labeled imidocarb were dissolved in chloroform and the solution evaporated to dryness under vacuum. The resulting mixed residue was suspended in 5 ml of 0.154 M NaCl and 10 mM trihydroxymethylamine (pH 8.0) and the resulting suspension was sonicated for 15 minutes at 51° C. under a nitrogen atmosphere. The liquid was then chromatographed on a $2.5 \times 40$ cm Sepharose 4B gel column and the fractions showing a coincidence of the $^{14}$C-labeled imidocarb, phospholipids and cholesteryl oleate were pooled and concentrated by ultrafilatration to a final concentration of 0.6 mg of imidocarb per mil.

A solution of free imidocarb at a concentration of 0.6 mg/ml in 0.154 M NaCl and 10 mM of trihydroxymethylamine (pH 8.0) was also prepared as a control to be used in free imidocarb administration.

The imidocarb-containing microreservoirs and free imidocarb were injected into the tail veins of rats at two dosage levels, i e., 5 mg/kg, and 4.4 mg/kg. Plasma samples were taken at various time points and the amount of imidocarb in these samples was determined by measurements of their radio-activity. The results of these measurements, plotted as imidocarb equivalents as a function of time, are given in FIGS. 23 and 24.

The beneficial alteration of the plasma kinetics through the use of the circulating microreservoirs to carry imidocarb in the bloodstream of a living mammalian host is clearly evident from FIGS. 23 and 24. For example, at a dosage level of 5 mg/kg, the concentration of the imidocarb in the microreservoirs/imidocarb in the bloodstream was about 140 times greater than the free imidocarb after four hours; and at a dosage level of 4.4 mg/kg about 200 times greater after this same period of time. Moreover, as noted on FIG. 24, the bloodstream still contained a measurable quantity of imidocarb in the microreservoir/imidocarb form after 24 hours as contrasted with virtually none in the free form of imidocarb.

The ratio of imidocarb to microreservoirs as a function of time is also plotted for each dosage level in FIGS. 23 and 24; and these plots clearly show that the drug is released at a rate which can be controlled and predetermined for any given set of conditions. From FIGS. 23 and 24 it is also apparent that it is possible, if desired, to reduce the dosage levels of the drug to far below those now considered effective in killing the blood-borne parasites which cause anaplasma in animals.

One of the major goals in beneficially altering the pharmacodynamics of a xenobiotics is the ability to alter the tissue distribution of the xenobiotic. That this can be achieved for imidocarb using the microreservoirs of this invention is shown in Example 19 and Table 3.

EXAMPLE 19

The animals used in Example 18 were sacrificed at 4 hours after the injection of free imidocarb or the microreservoirs containing imidocarb. Various tissues, such as muscle, spleen, liver and kidney, were taken from the animals. These tissues were combusted in a Searle combustion apparatus and the resulting $^{14}CO_2$ was collected and counted for radioactivity. The number of counts per gram of tissue was determined and the results are shown in Table 2.

TABLE 2

TISSUE DISTRIBUTION OF FREE IMIDOCARB AND MICRORESERVOIR-BORNE IMIDOCARB

| | dpm/gram of tissue | | |
|---|---|---|---|
| Tissue | Imidocarb | Microreservoir/ Imidocarb | Percent Change |
| Muscle | 3,985 | 3,511 | −12 |
| Kidney | 40,194 | 59,984 | +49 |
| Spleen | 9,498 | 15,339 | +61 |
| Liver | 27,059 | 29,991 | +11 |

The ability to maintain a xenobiotic in the bloodstream and within certain organs is particularly significant for a drug such as imidocarb. Thus, the 12% reduction of imidocarb in muscle tissue attained through the use of the microreservoirs is important to the use of this paraciticide in treating animals to be used for human consumption. Moreover, the greater concentration of the drug in the liver and spleen, organs which contain a greater proportion of the anaplasma microorganism, is another significant parameter in exploiting the use of imidocarb.

Among the pharmacodynamics of a xenobiotic which may be beneficially altered by the delivery vehicle of this invention is oral absorption, the altering being achieved by imparting to the xenobiotic the ability to cross the gastrointestinal (GI) tract and enter into the bloodstream for effective circulation. At present, several solutions are available for administering xenobiotics which do not cross the GI tract, or which cross it to a very limited degree, into the bloodstream. One such solution lies in the chemical modification of the xenobiotic, such as forming the undecanoate ester of estradiol which is essentially insoluble in water and suspending it in oil, forming it into a microcrystalline dispersion, or making a solution with an organic solvent such as ethanol.

The incorporation of estradiol undecanoate (used as a fertility control agent) in microreservoirs in accordance with this invention eliminates the need for such liquid media as oils and organic solvents and at the same time achieves a much more satisfactory discharge of this xenobiotic into the bloodstream. The incorporation of estradiol undecanoate in the microreservoirs of this invention is shown in Example 20 and FIG. 25.

EXAMPLE 20

300 μmoles of egg yolk phosphatidyl choline, 30 μmoles of cholesteryl oleate and 6 μmoles of $^3H$-labeled estradiol undecanoate (specific activity 4.6 μCi/μmole) were dissolved in benzene and lyophillized. To the resulting dry mixture were then added 5 ml of 0.154 M NaCl and 5 mM trihydroxymethylamine; and the resulting liquid was sonicated for 17 minutes at 48° C. under a nitrogen atmosphere. The resulting sonicated mixture was then fractionated by chromatographing it on a Sepharose 4B column to produce the elution profile of FIG. 25. Fractions 12-30 constituted the xenobiotic-containing vesicular microreservoirs used in making an in vivo evaluation of the delivery vehicle of this invention.

The ability of the microreservoirs of this invention to enhance the oral absorption of estradiol undecanoate is further illustrated in Example 21, FIG. 26 and Table 3.

EXAMPLE 21

$^3H$-labeled estradiol undecanoate was encapsulated in microreservoirs composed of egg yolk posphatidyl choline and $^{14}C$-labeled cholesteryl oleate. Equivalent amounts of $^3H$-labeled estradiol undecanoate were dissolved in ethanol. Doses of 1.63 mg/kg were administered orally to two sets of 9 rats. After 1, 4 and 24 hours, three of the rats in each set were killed and the blood collected. The plasma was separated from the red cells by centrifugation and 0.5 ml of each plasma sample was added to 9.5 ml of $CHCl_3$/MeOH (2/1 by volume) containing 1.6 μmoles of unlabeled estradiol and estrone as carriers. The resulting liquid was filtered and sufficient saline was added to the filtrates to make a 2-phase system. The lower phase was taken to dryness and then redissolved in 2.0 ml of methanol. 0.2 ml of this solution was counted for radioactivity. The remaining 1.8 ml was spotted on a TLC plate and developed in benzene/ethyl acetate (3/2 by volume). The plates were exposed briefly to iodine vapor to allow the carrier steroids to become visualized and then iodine vapor was driven off by mild heating. Those spots corresponding to estradiol and estrone were cut out and counted for radioactivity. The equivalents of $^3H$ estradiol undecanoate in the plasma are plotted in FIG. 26. It can be seen that by the first hour the vesicular microreservoirs enhanced the appearance of $^3H$-labeled estradiol undecanoate equivalents in the plasma when compared with the ethanol-control solution. After four hours, the amount of estradiol undecanoate equivalents was decreased for both formulations.

It is known that estradiol is the active form of the drug, and estrone is inactive. Furthermore, the esters of estradiol are assumed to be inactive until hydrolyzed to estradiol. Therefore, the ratio of estradiol to estrone in plasma should be an index of the ability of the microreservoirs to enhance the active form of the drug.

The results of the TLC analysis of the labeled estradiol derivatives in the plasma are given in Table 3. It can be seen from these data that the ratio of estradiol to estrone is higher by 60% using the microreservoirs than using an ethanol solution.

TABLE 3

RATIO OF $^3$H ESTRADIOL TO $^3$H ESTRONE IN PLASMA ONE HOUR AFTER ORAL ADMINISTRATION OF ESTRADIOL UNDECANOATE

| Formulation | Estradiol/Estrone* |
|---|---|
| In ethanol solution | 1.14 |
| In microreservoirs | 1.84 |

*Ratio is based on average of three rats.

The microreservoir delivery system of this invention also offers the possibility of orally administering xenobiotics heretofore incapable of this mode of administration. By transporting such drugs across the GI tract it is possible to deliver them to the bloodstream indirectly, thus eliminating their metabolism in the GI tract and the need for injections and the trouble and complications attendant on this form of administration.

The microreservoirs may be used in either their vesicular form or nonvesicular form or in a combination of these forms. This is illustrated by Example 22 and FIGS. 27 and 28.

EXAMPLE 22

25 μmoles of egg phosphatidyl choline, 75 μmoles of $^{14}$C-labeled cholesteryl oleate, and 2 μmoles of $^3$H-labeled estradiol undecanoate were dissolved in chloroform and taken to dryness. The lipid mixture was dried overnight under vacuum and then hydrated with 4.4 ml of 0.154 M NaCl and 5 mM trihydroxymethylamine (pH 7.2). The resulting liquid was sonicated at 40° C. for 20 minutes under a nitrogen atmosphere and passed down a Sepharose 4B Column. The resulting elution profile is shown in FIG. 27. It can be observed that the estradiol undecanoate has a higher affinity for the vesicular form of the microreservoirs than for the nonvesicular form, based on the ratio of estradiol undecanoate to cholesteryl oleate in the two forms of the microreservoirs. The material in the void volume of the column consisted of the nonvesicular form, whereas the material in the internal volume consisted of the vesicular form.

Samples of both the nonvesicular and vesicular forms containing estradiol undecanoate and approximately one μmole of total lipid were incubated with 9 μmoles of an unsonicated egg phosphatidyl choline dispersion. At various time points the samples were centrifuged at 15,000 g for 2 minutes and the supernatant containing the microreservoirs was counted for radioactivity. Since the cholesteryl oleate is a nonexchangeable species in this system, the ratio of $^3$H-labeled estradiol undecanoate to $^{14}$C-labeled cholesteryl oleate is an indication of the rate of efflux of estradiol undecanoate from the nonvesicular or vesicular microreservoirs to the phosphatidyl choline dispersion. The results are shown in FIG. 28. It will be seen that the estradiol undecanoate remained associated with both forms of the microreservoirs, indicating that both are satisfactory for carrying and releasing xenobiotics.

The xenobiotic-containing microreservoirs of this invention may be formulated into a variety of dosage forms. Thus, for example, they may be dispersed in a physiologically compatible liquid, they may be used dry to form tablets, or they may be contained in capsules formed of a suitable biocompatible material.

From the detailed description and examples given, it will be seen that the delivery vehicle of this invention is capable of beneficially altering the pharmacodynamics of xenobiotics having a wide range of chemical and physical characteristics as well as a wide range of biological uses and properties.

It will thus be seen that the objects set forth above, among those made apparent from the preceding description, are efficiently attained and, since certain changes may be made in carrying out the above method and in the composition and article set forth without departing from the scope of the invention, it is intended that all matter contained in the above description or shown in the accompanying drawings shall be interpreted as illustrative and not in a limiting sense.

We claim:

1. A delivery vehicle incorporating a xenobiotic and being biocompatible with a mammalian host to deliver and release within the aqueous environment of said host said xenobiotic the pharocodynamics of which are beneficially altered by reason of its delivery by and release from said vehicle, said delivery vehicle being in the form of microreservoirs in nonvesicular form having diameters ranging between about 250 Å and about 1000 Å, vesicular form having diameters ranging between about 190 Å and about 300 Å, or both nonvesicular and vesicular form comprising a phospholipid constituent and a phospholipid-immiscible lipid constituent present in an amount exceeding that which is miscible with said phospholipid constituent thereby imparting to said delivery vehicle a structure in which contact between said phospholipid-immiscible lipid constituent and said aqueous environment is minimized to impart to said delivery vehicle in vitro and in vivo stability, thereby providing for the controlled release of said xenobiotic therefrom.

2. A delivery vehicle in accordance with claim 1 wherein said microreservoirs are in vesicular form having diameters ranging between about 190 Å and about 300 Å.

3. A delivery vehicle in accordance with claim 1 wherein said microreservoirs are in nonvesicular form having diameters ranging between about 250 Å and about 1000 Å.

4. A delivery vehicle in accordance with claim 1 wherein said microreservoirs are in both nonvesicular and vesicular forms.

5. A delivery vehicle in accordance with claim 1 wherein said microreservoirs comprise between about 50 mole % and about 97 mole % of said phospholipid constituent.

6. A delivery vehicle in accordance with claim 1 wherein said microreservoirs comprises a xenobiotic binding modifier.

7. A delivery vehicle in accordance with claim 1 wherein said xenobiotic binding modifier is phosphatidic acid forming a minor portion of said phospholipid constituent.

8. A delivery vehicle in accordance with claim 1 wherein said xenobiotic binding modifier is cholesterol.

9. A delivery vehicle in accordance with claim 1 wherein said microreservoirs comprises a xenobiotic release-rate control agent.

10. A delivery vehicle in accordance with claim 9 wherein said xenobiotic release-rate control agent is a lipid miscible with said phospholipid constituent of said microreservoirs.

11. A delivery vehicle in accordance with claim 10 wherein said lipid is cholesterol.

12. A delivery vehicle in accordance with claim 1 wherein said phospholipid constituent comprises phosphatidyl choline.

13. A delivery vehicle in accordance with claim 1 wherein said phospholipid constituent comprises a mixture of phosphatidyl choline and phosphatidic acid, said phosphatidic acid being present in said mixture in an amount equivalent to at least about 5 mole %.

14. A delivery vehicle in accordance with claim 1 wherein said phospholipid-immiscible lipid constituent comprises a cholesterol ester of a fatty acid having between 10 and 18 carbon atoms.

15. A delivery vehicle in accordance with claim 14 wherein said cholesterol ester is cholesteryl oleate.

16. A delivery vehicle in accordance with claim 1 wherein said phospholipid-immiscible lipid constituent comprises a triglyceride.

17. A delivery vehicle in accordance with claim 16 wherein said triglyceride is glycerol trioleate.

18. A delivery vehicle in accordance with claim 1 wherein said xenobiotic is a drug.

19. A delivery vehicle in accordance with claim 18 wherein said drug is a chemotherapeutic drug.

20. A delivery vehicle in accordance with claim 19 wherein said drug is a cancer chemotherapeutic drug.

21. A delivery vehicle in accordance with claim 20 wherein said cancer chemotherapeutic drug is an anthracycline.

22. A delivery vehicle in accordance with claim 21 wherein said cancer chemotherapeutic drug is daunomycin.

23. A delivery vehicle in accordance with claim 21 wherein said cancer chemotherapeutic is adriamycin.

24. A delivery vehicle in accordance with claim 21 wherein said cancer chemotherapeutic drug is N-trifluoroacetyladriamycin-14-valerate.

25. A delivery vehicle in accordance with claim 18 wherein said drug is a parasiticide.

26. A delivery vehicle in accordance with claim 25 wherein said parasiticide is imidocarb.

27. A delivery vehicle in accordance with claim 18 wherein said drug is a fertility control agent.

28. A delivery vehicle in accordance with claim 27 wherein said fertility control agent is estradiol undecanoate.

29. A delivery vehicle in accordance with claim 1 wherein said xenobiotic is a drug, the plasma kinetics of which are beneficially altered.

30. A delivery vehicle in accordance with claim 1 wherein said xenobiotic is a drug, the chemotherapeutic effectiveness of which is beneficially altered.

31. A delivery vehicle in accordance with claim 1 wherein said xenobiotic is a drug, the toxicity of which is beneficially altered.

32. A delivery vehicle in accordance with claim 1 wherein said xenobiotic is a drug, the oral absorption, and hence its ability to pass the gastrointestinal tract, is beneficially altered.

33. A method of forming a delivery vehicle for delivering to and releasing within the aqueous environment of a mammalian host a xenobiotic, the pharmocodynamics of which are predeterminably altered and controlled comprising forming microreservoirs of a composition comprising a phospholipid constituents and a phospholipid-immiscible lipid constituent present in an amount exceeding that which is miscible with said phospholipid constituent to form said microreservoirs having a structure in which contact between said phospholipid-immiscible lipid constituent and said aqueous environment is minimized to impart to said delivery vehicle said microreservoirs being in nonvesicular form having diameters ranging between about 250 Å and about 1000 Å, vesicular form having diameters ranging between about 190 Å and about 300 Å, or both nonvesicular and vesicular forms.

34. A method in accordance with claim 33 wherein said step of forming said microreservoirs comprises
 (a) forming with a solvent a solution of said phospholipid constituent and of said phospholipid-immiscible lipid constituent;
 (b) removing said solvent to produce a dry residue mixture of said phospholipid constituent and said phospholipid-immiscible lipid constituent;
 (c) hydrating said dry residue mixture with a physiologically-compatible liquid to form a suspension;
 (d) sonicating said suspension under a nonoxidizing atmosphere at a temperature at least equivalent to the melting point of said phospholipid-immiscible lipid constituent to form said microreservoirs; and
 (e) separating out said microreservoirs thus formed.

35. A method in accordance with claim 34 wherein said step of incorporating said xenobiotic within said microreservoirs comprises adding said xenobiotic to said solution in step (a).

36. A method in accordance with claim 34 wherein said step of incorporating said xenobiotic within said microreservoirs comprises adding said xenobiotic to said suspension of step (c) prior to said sonicating.

37. A method in accordance with claim 34 wherein said step of separating out said microreservoirs thus formed comprises centrifuging the sonicated suspension and chromatographing the clear phase resulting from said centrifuging to provide a series of chromatographed fractions.

38. A method in accordance with claim 37 further including the step of separating those of said chromatographed fractions containing said microreservoirs in vesicular form having diameters ranging between about 190 Å and 300 Å from those fractions containing said microreservoirs in nonvesicular form having diameter ranging between about 250 Å and about 1000 Å.

39. A method in accordance with claim 34 including the step of adding a xenobiotic binding modifier to said solution.

40. A method in accordance with claim 33 wherein said xenobiotic binding modifier is phosphatidic acid forming a minor portion of said phospholipid constituent.

41. A method in accordance with claim 33 wherein said xenobiotic binding modifier is cholesterol.

42. A method in accordance with claim 34 including the step of adding a xenobiotic release-rate control agent to said solution.

43. A method in accordance with claim 42 wherein said xenobiotic release-rate control agent is a lipid miscible with said phospholipid-constituent of said microreservoirs.

44. A method in accordance with claim 33 wherein said phospholipid constituent comprises phosphatidyl choline.

45. A method in accordance with claim 33 wherein said phospholipid constituent comprises a mixture of phosphatidyl choline and phosphatidic acid, said phosphatidic acid being present in said mixture in an amount equivalent to at least about 5 mole %.

46. A method in accordance with claim 33 wherein said phospholipid-immiscible lipid constituent comprises a cholesterol ester of a fatty acid having between 10 and 18 carbon atoms.

47. A method in accordance with claim 46 wherein said cholesterol ester is cholesteryl oleate.

48. A method in accordance with claim 33 wherein said phospholipid-immiscible lipid constituent comprises a triglyceride.

49. A method in accordance with claim 48 wherein said triglyceride is glycerol trioleate.

50. A method in accordance with claim 33 wherein said xenobiotic is a drug.

51. A method in accordance with claim 50 wherein said drug is a chemotherapeutic drug.

52. A method in accordance with claim 51 wherein said drug is a cancer chemotherapeutic drug.

53. A method in accordance with claim 52 wherein said cancer chemotherapeutic drug is an anthracycline.

54. A method in accordance with claim 52 wherein said cancer chemotherapeutic drug is daunomycin.

55. A method in accordance with claim 53 wherein said cancer chemotherapeutic drug is adriamycin.

56. A method in accordance with claim 53 wherein said cancer chemotherapeutic drug is N-trifluoroacetyladriamycin-14-valerate.

57. A method in accordance with claim 50 wherein said drug is a parasiticide.

58. A method in accordance with claim 57 wherein said parasiticide is imidocarb.

59. A method in accordance with claim 50 wherein said drug is a fertility control agent.

60. A method in accordance with claim 59 wherein said fertility control agent is estradiol undecanoate.

61. A method in accordance with claim 33 wherein said xenobiotic is a drug, the plasma kinetics of which are beneficially altered.

62. A method in accordance with claim 33 wherein said xenobiotic is a drug, the chemotherapeutic effectiveness of which is beneficially altered.

63. A method in accordance with claim 33 wherein said xenobiotic is a drug, the toxicity of which is beneficially altered.

64. A method in accordance with claim 33 wherein said xenobiotic is a drug, the oral absorption, and hence its ability to pass the gastrointestinal tract, is beneficially altered.

65. A method in accordance with claim 33 wherein said step of forming said microreservoirs comprises
(1) forming in a water-miscible organic solvent a solution of said phospholipid constituent and said phospholipid-immiscible lipid constituent;
(2) injecting said solution into said physiologically-compatible liquid under conditions to form said microreservoirs.

66. A method in accordance with claim 65 wherein said step of incorporating said xenobiotic within said microreservoirs comprises adding said xenobiotic to said solution.

67. A method in accordance with claim 65 wherein said step of incorporating said xenobiotic within said microreservoirs comprises adding said xenobiotic to said physiologically-compatible liquid.

68. A method in accordance with claim 33 including the step of suspending said microreservoirs containing said xenobiotic in a physiologically-compatible liquid thereby providing said xenobiotic in liquid dosage form.

69. A method in accordance with claim 33 including the step of encapsulating said microreservoirs containing said xenobiotic in a capsule formed of a physiologically-acceptable material.

70. A method of controllably delivering to and releasing a xenobiotic within the aqueous environment of a mammalian host, comprising introducing into said mammalian host a pharmaceutically effective amount of a xenobiotic contained within microreservoirs, said microreservoirs being in nonvesicular form having diameters ranging between about 250 Å and about 1000 Å, vesicular form having diameters ranging between about 190 Å and about 300 Å or both nonvesicular and vesicular forms and formed of a phospholipid constituent and a phospholipid-immiscible lipid constituent present in an amount exceeding that which is miscible with said phospholipid constituent thereby imparting to said delivery vehicle a structure in which contact between said phospholipid immiscible lipid constituent and said aqueous environment is minimized to impart to said microreservoirs in vitro and in vivo stability, thereby providing for the controlled release of said xenobiotic therefrom.

71. A method in accordance with claim 70 wherein said microreservoirs are in vesicular form having diameters ranging between about 190 Å and about 300 Å.

72. A method in accordance with claim 70 wherein said microreservoirs are in nonvesicular form having diameters ranging between about 250 Å and about 1000 Å.

73. A method in accordance with claim 70 wherein said microreservoirs are in both nonvesicular and vesicular forms.

74. A method in accordance with claim 70 wherein said microreservoirs comprise between about 50 mole % and about 97 mole % of said phospholipid constituent.

75. A method in accordance with claim 70 wherein said microreservoirs comprises a xenobiotic binding modifier.

76. A method in accordance with claim 75 wherein said xenobiotic binding modifier is phosphatidic acid forming a minor portion of said phospholipid constituent.

77. A method in accordance with claim 75 wherein said xenobiotic binding modifier is cholesterol.

78. A method in accordance with claim 76 wherein said microreservoirs comprises a xenobiotic release-rate control agent.

79. A method in accordance with claim 78 wherein said xenobiotic relase-rate control agent is a lipid miscible with said phospholipid constituent of said microreservoirs.

80. A method in accordance with claim 70 wherein said phospholipid constituent comprises phosphatidyl choline.

81. A method in accordance with claim 70 wherein said phospholipid constituent comprises a mixture of phosphatidyl choline and phosphatidic acid, said phosphatidic acid being present in said mixture in an amount equivalent to at least about 5 mole %.

82. A method in accordance with claim 70 wherein said phospholipid-immiscible lipid constituent comprises a cholesterol ester of a fatty acid having between 10 and 18 carbon atoms.

83. A method in accordance with claim 82 wherein said cholesterol ester is cholesteryl oleate.

84. A method in accordance with claim 70 wherein said phospholipid-immiscible lipid constituent comprises a triglyceride.

85. A method in accordance with claim 84 wherein said triglyceride is glycerol trioleate.

86. A method in accordance with claim 70 wherein said step of introducing said xenobiotic contained within said microreservoirs into said mammalian host comprises suspending said microreservoirs in a physiologically-compatible liquid.

87. A method in accordance with claim 86 wherein said physiologically-compatible liquid is a saline solution.

88. A method in accordance with claim 86 wherein said physiologically-compatible liquid is a dilute aqueous solution of KCl.

89. A method in accordance with claim 70 wherein said xenobiotic is a drug.

90. A method in accordance with claim 89 wherein said drug is a chemotherapeutic drug.

91. A method in accordance with claim 90 wherein said drug is a cancer chemotherapeutic drug.

92. A method in accordance with claim 91 wherein said cancer chemotherapeutic drug is an anthracycline.

93. A method in accordance with claim 92 wherein said cancer chemotherapeutic drug is daunomycin.

94. A method in accordance with claim 92 wherein said cancer chemotherapeutic drug is adriamycin.

95. A method in accordance with claim 92 wherein said cancer chemotherapeutic drug is N-trifluoroacetyladriamycin-14-valerate.

96. A method in accordance with claim 89 wherein said drug is a parasiticide.

97. A method in accordance with claim 96 wherein said parasiticide is imidocarb.

98. A method in accordance with claim 89 wherein said drug is a fertility control agent.

99. A method in accordance with claim 98 wherein said fertility control agent is estradiol undecanoate.

100. A method in accordance with claim 70 wherein said step of introducing said xenobiotic contained within said microreservoirs into said mammalian host comprises administering orally, topically or by inhalation, or by intravenous, intramuscular, interperitoneal or subcutaneous injection.

101. A method in accordance with claim 70 wherein said microreservoirs containing said xenobiotic are contained within a tablet or a capsule and said step of introducing into said mammalian host comprises administering said tablet or said capsule orally.

102. A method of controlling the pharmacodynamics under which a xenobiotic is delivered within the aqueous environment of a mammalian host, comprising the step of releasing said xenobiotic within said host from circulating microreservoirs, said microreservoirs being in nonvesicular form having diameters ranging between about 250 Å and about 1000 Å, vesicular form having diameters ranging between about 190 Å and about 300 Å on both nonvesicular and vesicular form and formed of a phospholipid constituent and a phospholipid-immiscible lipid constituent present in an amount exceeding that which is miscible with said phospholipid constituent thereby imparting to said delivery vehicle a structure in which contact between said phospholipid-immiscible lipid constituent and said aqueous environment is minimized to impart to said microreservoirs in vitro and in vivo stability, thereby controlling said pharmacodynamics of said xenobiotic.

103. A method in accordance with claim 102 wherein said xenobiotic is a drug.

104. A delivery vehicle in accordance with claim 103 wherein said drug is a parasiticide.

105. A delivery vehicle in accordance with claim 103 wherein said parasiticide is imidocarb.

106. A method in accordance with claim 102 wherein said drug is a cancer chemotherapeutic drug.

107. A method in accordance with claim 106 wherein said cancer chemotherapeutic drug is an anthracycline.

108. A method in accordance with claim 107 wherein said cancer chemotherapeutic drug is daunomycin.

109. A method in accordance with claim 107 wherein said cancer chemotherapeutic drug is adriamycin.

110. A method in accordance with claim 107 wherein said cancer chemotherapeutic drug is N-trifluoroacetyladriamycin-14-valerate.

111. A method in accordance with claim 102 wherein said xenobiotic is a fertility control agent.

112. A method in accordance with claim 111 wherein said fertility control agent is estradiol undecanoate.

113. A method in accordance with claim 102 wherein said circulating microreservoirs are in vesicular form having diameters ranging between about 190 Å and about 300 Å.

114. A method in accordance with claim 102 wherein said circulating microreservoirs are in nonvesicular form having diameters ranging between about 250 Å and about 1000 Å.

115. A method in accordance with claim 102 wherein said circulating microreservoirs are in both nonvesicular and vesicular forms.

116. A method in accordance with claim 102 wherein said circulating microreservoirs comprise between about 50 mole % and about 97 mole % of said phospholipid constituent.

117. A method in accordance with claim 102 wherein said circulating microreservoirs comprises a xenobiotic binding modifier.

118. A method in accordance with claim 117 wherein said xenobiotic binding modifier is phosphatidic acid forming a minor portion of said phospholipid constituent.

119. A method in accordance with claim 117 wherein said xenobiotic binding modifier is cholesterol.

120. A method in accordance with claim 102 wherein said circulating microreservoirs comprises a xenobiotic release-rate control agent.

121. A method in accordance with claim 120 wherein said xenobiotic release-rate control agent is a lipid-miscible with said phospholipid constituent of said microreservoirs.

122. A method in accordance with claim 121 wherein said lipid is cholesterol.

123. A method in accordance with claim 102 wherein said phospholipid constituent comprises phosphatidyl choline.

124. A method in accordance with claim 102 wherein said phospholipid constituent comprises a mixture of phosphatidyl choline and phosphatidic acid, said phosphatidic acid being present in said mixture in an amount equivalent to at least about 5 mole %.

125. A method in accordance with claim 102 wherein said phospholipid-immiscible lipid constituent comprises a cholesterol ester of a fatty acid having between 10 and 18 carbon atoms.

126. A method in accordance with claim 125 wherein said cholesterol ester is cholesteryl oleate.

127. A method in accordance with claim 102 wherein said phospholipid-immiscible lipid constituent comprises a triglyceride.

128. A method in accordance with claim 127 wherein said triglyceride is glycerol trioleate.

* * * * *